(12) United States Patent
O'Neil et al.

(10) Patent No.: US 12,426,868 B2
(45) Date of Patent: Sep. 30, 2025

(54) BALLOON WITH SHAPE CONTROL FOR SPINAL PROCEDURES

(71) Applicant: DePuy Synthes Products, Inc., Raynham, MA (US)

(72) Inventors: Michael J. O'Neil, West Barnstable, MA (US); Michael Andrew Slivka, Taunton, MA (US); Anwar M. Upal, Fall River, MA (US); John Riley Hawkins, Cumberland, RI (US); Michael Alan Fisher, Lawrenceville, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 875 days.

(21) Appl. No.: 17/029,710

(22) Filed: Sep. 23, 2020

(65) Prior Publication Data
US 2021/0015474 A1    Jan. 21, 2021

Related U.S. Application Data

(63) Continuation of application No. 15/912,286, filed on Mar. 5, 2018, now Pat. No. 10,786,231, which is a
(Continued)

(51) Int. Cl.
*A61B 17/02* (2006.01)
*A61B 17/88* (2006.01)
(Continued)

(52) U.S. Cl.
CPC ........ *A61B 17/025* (2013.01); *A61B 17/8805* (2013.01); *A61F 2/442* (2013.01);
(Continued)

(58) Field of Classification Search
CPC . A61B 17/025; A61B 17/8805; A61B 17/885; A61B 17/8855; A61B 17/8858;
(Continued)

(56) References Cited

U.S. PATENT DOCUMENTS

| 4,573,448 A | 3/1986 | Kambin |
| 4,646,738 A | 3/1987 | Trott |

(Continued)

FOREIGN PATENT DOCUMENTS

| CN | 102727309 B | 11/2014 |
| DE | 9415039 U1 | 11/1994 |

(Continued)

OTHER PUBLICATIONS

International Search Report and Written Opinion for Application No. PCT/US2015/043554, mailed Nov. 19, 2015 (8 pages).
(Continued)

*Primary Examiner* — Tracy L Kamikawa
(74) *Attorney, Agent, or Firm* — Barnes & Thornburg LLP

(57) ABSTRACT

Devices and methods for minimally invasive disc space distraction and implantation are provided. For example, in intervertebral operative spinal procedures, separate or pre-attached spreader blocks can be used to control the directional growth of a distracting balloon. The spreader blocks can provide an initial distraction of the disc space while the distracting balloon provides further distraction of the disc space. When distraction is achieved, an intervertebral implant may be inserted into the distracted disc space. After the implant is firmly implanted, the balloon and spreader block may be removed.

14 Claims, 21 Drawing Sheets

Related U.S. Application Data continuation of application No. 15/218,131, filed on Jul. 25, 2016, now Pat. No. 9,936,938, which is a continuation of application No. 14/925,615, filed on Oct. 28, 2015, now Pat. No. 9,421,056, which is a continuation of application No. 11/863,839, filed on Sep. 28, 2007, now abandoned.

(51) Int. Cl.
| | | |
|---|---|---|
| *A61F 2/44* | (2006.01) | |
| *A61M 29/02* | (2006.01) | |
| *A61B 17/00* | (2006.01) | |
| *A61M 25/10* | (2013.01) | |

(52) U.S. Cl.
CPC ... *A61M 29/02* (2013.01); *A61B 2017/00557* (2013.01); *A61B 2017/0225* (2013.01); *A61B 2017/0256* (2013.01); *A61M 25/1002* (2013.01); *A61M 2025/1063* (2013.01)

(58) Field of Classification Search
CPC .. A61B 2017/00557; A61B 2017/0225; A61B 2017/0256; A61F 2/442; A61M 29/02; A61M 25/1002; A61M 2025/1063
See application file for complete search history.

(56) References Cited

U.S. PATENT DOCUMENTS

| | | | |
|---|---|---|---|
| 4,678,459 | A | 7/1987 | Onik et al. |
| 4,863,430 | A | 9/1989 | Klyce et al. |
| 4,863,476 | A | 9/1989 | Shepperd |
| 4,888,146 | A | 12/1989 | Dandeneau |
| 5,080,662 | A | 1/1992 | Paul |
| 5,123,926 | A | 6/1992 | Pisharodi |
| 5,163,949 | A | 11/1992 | Bonutti |
| 5,195,541 | A | 3/1993 | Obenchain |
| 5,285,795 | A | 2/1994 | Ryan et al. |
| 5,304,141 | A | 4/1994 | Johnson et al. |
| 5,374,267 | A | 12/1994 | Siegal |
| 5,395,317 | A | 3/1995 | Kambin |
| 5,439,464 | A | 8/1995 | Shapiro |
| 5,522,899 | A | 6/1996 | Michelson |
| 5,529,580 | A | 6/1996 | Kusunoki et al. |
| 5,540,706 | A | 7/1996 | Aust et al. |
| 5,569,290 | A | 10/1996 | McAfee |
| 5,591,187 | A | 1/1997 | Dekel |
| 5,601,569 | A | 2/1997 | Pisharodi |
| 5,662,300 | A | 9/1997 | Michelson |
| 5,665,122 | A | 9/1997 | Kambin |
| 5,688,222 | A | 11/1997 | Hluchy et al. |
| 5,730,754 | A | 3/1998 | Obenchain |
| 5,733,242 | A | 3/1998 | Rayburn et al. |
| 5,735,792 | A | 4/1998 | Vanden Hoek et al. |
| 5,820,623 | A | 10/1998 | Ng |
| 5,830,188 | A | 11/1998 | Abouleish |
| 5,865,848 | A | 2/1999 | Baker |
| 5,885,300 | A | 3/1999 | Tokuhashi et al. |
| 5,894,369 | A | 4/1999 | Akiba et al. |
| 5,899,425 | A | 5/1999 | Corey, Jr. et al. |
| 5,954,635 | A | 9/1999 | Foley et al. |
| 6,030,406 | A | 2/2000 | Davis et al. |
| 6,033,105 | A | 3/2000 | Barker et al. |
| 6,045,579 | A | 4/2000 | Hochshuler et al. |
| 6,053,907 | A | 4/2000 | Zirps |
| 6,063,021 | A | 5/2000 | Hossain et al. |
| 6,110,182 | A | 8/2000 | Mowlai-Ashtiani |
| 6,126,689 | A | 10/2000 | Brett |
| 6,176,882 | B1 | 1/2001 | Biedermann et al. |
| 6,200,322 | B1 | 3/2001 | Branch et al. |
| 6,217,509 | B1 | 4/2001 | Foley et al. |
| 6,234,961 | B1 | 5/2001 | Gray |
| 6,248,110 | B1 | 6/2001 | Reiley et al. |
| 6,254,598 | B1 | 7/2001 | Edwards et al. |
| 6,283,966 | B1 | 9/2001 | Houfburg |
| 6,286,179 | B1 | 9/2001 | Byrne |
| 6,296,644 | B1 | 10/2001 | Saurat et al. |
| 6,322,498 | B1 | 11/2001 | Gravenstein et al. |
| 6,332,894 | B1 | 12/2001 | Stalcup et al. |
| 6,354,992 | B1 | 3/2002 | Kato |
| 6,371,968 | B1 | 4/2002 | Kogasaka et al. |
| 6,383,191 | B1 | 5/2002 | Zdeblick et al. |
| 6,387,130 | B1 | 5/2002 | Stone et al. |
| 6,413,278 | B1 | 7/2002 | Marchosky |
| 6,447,446 | B1 | 9/2002 | Smith et al. |
| 6,468,289 | B1 | 10/2002 | Bonutti |
| 6,547,776 | B1 | 4/2003 | Gaiser et al. |
| 6,558,386 | B1 | 5/2003 | Cragg |
| 6,558,407 | B1 | 5/2003 | Ivanko et al. |
| 6,575,899 | B1 | 6/2003 | Foley et al. |
| 6,579,281 | B2 | 6/2003 | Palmer et al. |
| 6,595,998 | B2 | 7/2003 | Johnson et al. |
| 6,607,544 | B1 | 8/2003 | Boucher et al. |
| 6,626,830 | B1 | 9/2003 | Califiore et al. |
| 6,632,235 | B2 | 10/2003 | Weikel et al. |
| 6,648,915 | B2 | 11/2003 | Sazy |
| 6,676,597 | B2 | 1/2004 | Guenst et al. |
| 6,688,564 | B2 | 2/2004 | Salvermoser et al. |
| 6,706,069 | B2 * | 3/2004 | Berger ............ A61F 2/441 623/17.12 |
| 6,733,535 | B2 | 5/2004 | Michelson |
| 6,758,809 | B2 | 7/2004 | Briscoe et al. |
| 6,808,505 | B2 | 10/2004 | Kadan |
| 6,835,208 | B2 | 12/2004 | Marchosky |
| 6,887,198 | B2 | 5/2005 | Phillips et al. |
| 6,983,930 | B1 | 1/2006 | La Mendola et al. |
| 7,087,058 | B2 | 8/2006 | Cragg |
| 7,104,986 | B2 | 9/2006 | Hovda et al. |
| 7,137,949 | B2 | 11/2006 | Scirica et al. |
| 7,182,731 | B2 | 2/2007 | Nguyen et al. |
| 7,326,248 | B2 | 2/2008 | Michelson |
| 7,341,556 | B2 | 3/2008 | Shalman |
| 7,434,325 | B2 | 10/2008 | Foley et al. |
| 7,452,351 | B2 | 11/2008 | Miller et al. |
| 7,503,920 | B2 | 3/2009 | Siegal |
| 7,591,790 | B2 | 9/2009 | Pflueger |
| 7,594,888 | B2 | 9/2009 | Raymond et al. |
| 7,618,431 | B2 | 11/2009 | Roehm, III et al. |
| 7,632,294 | B2 | 12/2009 | Milbodker et al. |
| 7,636,596 | B2 | 12/2009 | Solar |
| 7,637,905 | B2 | 12/2009 | Saadat et al. |
| 7,641,659 | B2 | 1/2010 | Emstad et al. |
| 7,655,010 | B2 | 2/2010 | Serhan et al. |
| 7,666,226 | B2 | 2/2010 | Schaller |
| 7,670,374 | B2 | 3/2010 | Schaller |
| 7,703,727 | B2 | 4/2010 | Selness |
| 7,713,273 | B2 | 5/2010 | Krueger et al. |
| 7,731,751 | B2 | 6/2010 | Butler et al. |
| 7,771,384 | B2 | 8/2010 | Ravo |
| 7,785,368 | B2 | 8/2010 | Schaller |
| 7,794,456 | B2 | 9/2010 | Sharps et al. |
| 7,799,035 | B2 | 9/2010 | Krueger et al. |
| 7,799,081 | B2 | 9/2010 | McKinley |
| 7,811,303 | B2 | 10/2010 | Fallin et al. |
| 7,824,431 | B2 | 11/2010 | McCormack |
| 7,837,734 | B2 | 11/2010 | Zucherman et al. |
| 7,850,733 | B2 | 12/2010 | Baynham et al. |
| 7,918,874 | B2 | 4/2011 | Siegal |
| 7,931,579 | B2 | 4/2011 | Bertolero et al. |
| 7,942,903 | B2 | 5/2011 | Moskowitz et al. |
| 7,946,981 | B1 | 5/2011 | Cubb |
| 7,947,078 | B2 | 5/2011 | Siegal |
| 7,951,141 | B2 | 5/2011 | Sharps et al. |
| 7,959,564 | B2 | 6/2011 | Ritland |
| 7,988,623 | B2 | 8/2011 | Pagliuca et al. |
| 8,007,492 | B2 | 8/2011 | DiPoto et al. |
| 8,007,535 | B2 | 8/2011 | Hudgins et al. |
| 8,034,110 | B2 | 10/2011 | Garner et al. |
| 8,038,606 | B2 | 10/2011 | Otawara |
| 8,043,381 | B2 | 10/2011 | Hestad et al. |
| 8,057,544 | B2 | 11/2011 | Schaller |
| 8,062,218 | B2 | 11/2011 | Sebastian et al. |
| 8,088,119 | B2 | 1/2012 | Saal et al. |

(56) References Cited

U.S. PATENT DOCUMENTS

| | | | |
|---|---|---|---|
| 8,092,464 B2 | 1/2012 | McKay | |
| 8,096,944 B2 | 1/2012 | Harrel | |
| 8,105,382 B2 | 1/2012 | Olmos et al. | |
| 8,133,279 B2 | 3/2012 | Trieu | |
| 8,202,216 B2 | 6/2012 | Melkent et al. | |
| 8,206,423 B2 | 6/2012 | Siegal | |
| 8,236,006 B2 | 8/2012 | Hamada | |
| 8,236,029 B2 | 8/2012 | Siegal | |
| 8,241,328 B2 | 8/2012 | Siegal | |
| 8,246,622 B2 | 8/2012 | Siegal et al. | |
| 8,262,666 B2 | 9/2012 | Baynham et al. | |
| 8,267,939 B2 | 9/2012 | Cipoletti et al. | |
| 8,287,596 B1 | 10/2012 | Heim | |
| 8,328,812 B2 | 12/2012 | Siegal et al. | |
| 8,333,690 B2 | 12/2012 | Ikeda | |
| 8,343,193 B2 | 1/2013 | Johnson et al. | |
| 8,360,970 B2 | 1/2013 | Mangiardi | |
| 8,366,777 B2 | 2/2013 | Matthis et al. | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,403,990 B2 | 3/2013 | Dryer et al. | |
| 8,414,587 B2 | 4/2013 | Saal et al. | |
| 8,425,507 B2 | 4/2013 | Pellegrino et al. | |
| 8,435,174 B2 | 5/2013 | Cropper et al. | |
| 8,454,617 B2 | 6/2013 | Schaller et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,465,524 B2 | 6/2013 | Siegal | |
| 8,486,109 B2 | 7/2013 | Siegal | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,579,981 B2 | 11/2013 | Lim et al. | |
| 8,585,726 B2 | 11/2013 | Yoon et al. | |
| 8,597,330 B2 | 12/2013 | Siegal | |
| 8,602,979 B2 | 12/2013 | Kitano | |
| 8,622,894 B2 | 1/2014 | Banik et al. | |
| 8,636,655 B1 | 1/2014 | Childs | |
| 8,672,977 B2 | 3/2014 | Siegal et al. | |
| 8,690,764 B2 | 4/2014 | Clark et al. | |
| 8,721,536 B2 | 5/2014 | Marino et al. | |
| 8,740,779 B2 | 6/2014 | Yoshida | |
| 8,777,993 B2 | 7/2014 | Siegal et al. | |
| 8,784,421 B2 | 7/2014 | Carrison et al. | |
| 8,821,378 B2 | 9/2014 | Morgenstern Lopez et al. | |
| 8,827,981 B2 | 9/2014 | Liu et al. | |
| 8,834,507 B2 | 9/2014 | Mire et al. | |
| 8,845,638 B2 | 9/2014 | Siegal et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,894,658 B2 | 11/2014 | Linderman et al. | |
| 8,900,235 B2 | 12/2014 | Siegal | |
| 8,906,098 B2 | 12/2014 | Siegal | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,961,609 B2 | 2/2015 | Schaller | |
| 8,968,408 B2 | 3/2015 | Schaller et al. | |
| 8,974,381 B1 | 3/2015 | Lovell et al. | |
| 8,986,199 B2 | 3/2015 | Weisenburgh, II et al. | |
| 8,986,388 B2 | 3/2015 | Siegal et al. | |
| 8,992,580 B2 | 3/2015 | Bar et al. | |
| 9,017,408 B2 | 4/2015 | Siegal et al. | |
| 9,017,413 B2 | 4/2015 | Siegal et al. | |
| 9,028,522 B1 | 5/2015 | Prado | |
| 9,044,334 B2 | 6/2015 | Siegal et al. | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,095,393 B2 | 8/2015 | Schaus et al. | |
| 9,126,023 B1 | 9/2015 | Sahatjian et al. | |
| 9,131,948 B2 | 9/2015 | Fang et al. | |
| 9,144,374 B2 | 9/2015 | Maurice, Jr. | |
| 9,149,612 B2 | 10/2015 | Chuter | |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,232,935 B2 | 1/2016 | Brand et al. | |
| 9,241,806 B2 | 1/2016 | Suh | |
| 9,247,997 B2 | 2/2016 | Stefanchik et al. | |
| 9,254,138 B2 | 2/2016 | Siegal et al. | |
| 9,265,491 B2 | 2/2016 | Ins et al. | |
| 9,277,928 B2 | 3/2016 | Morgenstern Lopez | |
| 9,283,092 B2 | 3/2016 | Siegal et al. | |
| 9,307,972 B2 | 4/2016 | Lovell et al. | |
| 9,320,419 B2 | 4/2016 | Kirma et al. | |
| RE46,007 E | 5/2016 | Banik et al. | |
| RE46,062 E | 7/2016 | James et al. | |
| 9,386,971 B1 | 7/2016 | Casey et al. | |
| 9,387,313 B2 | 7/2016 | Culbert et al. | |
| 9,408,712 B2 | 8/2016 | Siegal et al. | |
| 9,414,828 B2 | 8/2016 | Abidin et al. | |
| 9,421,056 B2 | 8/2016 | O'Neil et al. | |
| 9,486,296 B2 | 11/2016 | Mire et al. | |
| 9,492,194 B2 | 11/2016 | Morgenstern Lopez et al. | |
| 9,510,853 B2 | 12/2016 | Aljuri et al. | |
| 9,526,401 B2 | 12/2016 | Saadat et al. | |
| 9,579,012 B2 | 2/2017 | Vazales et al. | |
| 9,603,510 B2 | 3/2017 | Ammirati | |
| 9,603,610 B2 | 3/2017 | Richter et al. | |
| 9,610,007 B2 | 4/2017 | Kienzle et al. | |
| 9,610,095 B2 | 4/2017 | To | |
| 9,629,521 B2 | 4/2017 | Ratnakar | |
| 9,655,605 B2 | 5/2017 | Serowski et al. | |
| 9,655,639 B2 | 5/2017 | Mark | |
| 9,668,643 B2 | 6/2017 | Kennedy, II et al. | |
| 9,675,235 B2 | 6/2017 | Lieponis | |
| 9,700,378 B2 | 7/2017 | Mowlai-Ashtiani | |
| 9,706,905 B2 | 7/2017 | Levy | |
| 9,936,938 B2* | 4/2018 | O'Neil | A61B 17/025 |
| 10,786,231 B2* | 9/2020 | O'Neil | A61B 17/8805 |
| 2002/0022762 A1 | 2/2002 | Beane et al. | |
| 2002/0026195 A1* | 2/2002 | Layne | A61B 17/3417 |
| | | | 606/92 |
| 2002/0138020 A1 | 9/2002 | Pflueger | |
| 2003/0028251 A1* | 2/2003 | Mathews | A61M 25/10 |
| | | | 623/23.62 |
| 2003/0083555 A1 | 5/2003 | Hunt et al. | |
| 2003/0135275 A1 | 7/2003 | Garcia et al. | |
| 2003/0139812 A1 | 7/2003 | Garcia et al. | |
| 2003/0171744 A1 | 9/2003 | Leung et al. | |
| 2003/0191474 A1 | 10/2003 | Cragg et al. | |
| 2003/0199979 A1* | 10/2003 | McGuckin, Jr. | A61F 2/442 |
| | | | 623/17.11 |
| 2003/0220649 A1 | 11/2003 | Bao et al. | |
| 2004/0002761 A1 | 1/2004 | Rogers et al. | |
| 2004/0073213 A1* | 4/2004 | Serhan | A61B 17/025 |
| | | | 606/279 |
| 2004/0087947 A1 | 5/2004 | Lim et al. | |
| 2004/0102774 A1 | 5/2004 | Trieu | |
| 2004/0122446 A1 | 6/2004 | Solar | |
| 2004/0127992 A1 | 7/2004 | Serhan et al. | |
| 2004/0133280 A1* | 7/2004 | Trieu | A61F 2/4611 |
| | | | 623/17.11 |
| 2004/0143165 A1 | 7/2004 | Alleyne | |
| 2004/0162559 A1 | 8/2004 | Arramon et al. | |
| 2004/0230309 A1* | 11/2004 | DiMauro | A61F 2/441 |
| | | | 623/17.11 |
| 2005/0070900 A1* | 3/2005 | Serhan | A61F 2/4611 |
| | | | 606/279 |
| 2005/0070913 A1 | 3/2005 | Milbocker et al. | |
| 2005/0085692 A1 | 4/2005 | Kiehn et al. | |
| 2005/0090846 A1 | 4/2005 | Pedersen et al. | |
| 2005/0090848 A1 | 4/2005 | Adams | |

(56) References Cited

U.S. PATENT DOCUMENTS

| | | |
|---|---|---|
| 2005/0090852 A1* | 4/2005 | Layne .................. A61F 2/4601 604/103.05 |
| 2005/0119752 A1 | 6/2005 | Williams et al. |
| 2005/0187570 A1 | 8/2005 | Nguyen et al. |
| 2005/0256525 A1 | 11/2005 | Culbert et al. |
| 2005/0288678 A1 | 12/2005 | Reiley et al. |
| 2006/0036241 A1 | 2/2006 | Siegal |
| 2006/0064101 A1 | 3/2006 | Arramon |
| 2006/0085070 A1 | 4/2006 | Kim |
| 2006/0122701 A1 | 6/2006 | Kiester |
| 2006/0142858 A1 | 6/2006 | Colleran et al. |
| 2006/0184192 A1* | 8/2006 | Markworth ........ A61B 17/1617 606/198 |
| 2006/0206118 A1 | 9/2006 | Kim et al. |
| 2006/0235426 A1 | 10/2006 | Lim et al. |
| 2006/0253199 A1* | 11/2006 | Lehuec ............. A61B 17/7097 623/17.12 |
| 2006/0264945 A1 | 11/2006 | Edidin et al. |
| 2006/0265076 A1 | 11/2006 | Carter et al. |
| 2007/0010846 A1 | 1/2007 | Leung et al. |
| 2007/0010848 A1 | 1/2007 | Leung et al. |
| 2007/0055259 A1 | 3/2007 | Norton et al. |
| 2007/0055272 A1 | 3/2007 | Schaller |
| 2007/0055276 A1* | 3/2007 | Edidin ................ A61B 17/8855 606/92 |
| 2007/0083225 A1 | 4/2007 | Kiser et al. |
| 2007/0093901 A1 | 4/2007 | Grotz et al. |
| 2007/0129634 A1 | 6/2007 | Hickey et al. |
| 2007/0149975 A1 | 6/2007 | Oliver et al. |
| 2007/0173785 A1 | 7/2007 | Ostroot |
| 2007/0203396 A1 | 8/2007 | McCutcheon et al. |
| 2007/0225556 A1 | 9/2007 | Ortiz et al. |
| 2007/0233245 A1* | 10/2007 | Trieu .................. A61F 2/4611 623/17.11 |
| 2007/0260113 A1 | 11/2007 | Otawara |
| 2007/0276491 A1 | 11/2007 | Ahrens et al. |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0108940 A1 | 5/2008 | Sharkey et al. |
| 2008/0133012 A1 | 6/2008 | McGuckin |
| 2008/0161927 A1 | 7/2008 | Savage et al. |
| 2008/0188714 A1 | 8/2008 | McCaffrey |
| 2008/0269756 A1 | 10/2008 | Tomko et al. |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0076610 A1 | 3/2009 | Afzal |
| 2009/0088789 A1 | 4/2009 | O'Neil et al. |
| 2009/0105543 A1 | 4/2009 | Miller et al. |
| 2009/0156898 A1 | 6/2009 | Ichimura |
| 2009/0182343 A1 | 7/2009 | Trudeau et al. |
| 2009/0187080 A1 | 7/2009 | Seex |
| 2009/0234457 A1 | 9/2009 | Lotz et al. |
| 2009/0240111 A1 | 9/2009 | Kessler et al. |
| 2009/0287061 A1 | 11/2009 | Feigenbaum et al. |
| 2009/0292287 A1 | 11/2009 | Cragg et al. |
| 2009/0318765 A1 | 12/2009 | Torii |
| 2010/0004651 A1 | 1/2010 | Biyani |
| 2010/0010530 A1 | 1/2010 | Rhee |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0137923 A1 | 6/2010 | Greenhalgh et al. |
| 2010/0151161 A1 | 6/2010 | Da Rolo |
| 2010/0152792 A1 | 6/2010 | Ralph et al. |
| 2010/0161060 A1 | 6/2010 | Schaller et al. |
| 2010/0168858 A1 | 7/2010 | Hardenbrook et al. |
| 2010/0256446 A1 | 10/2010 | Raju |
| 2010/0274188 A1 | 10/2010 | Chang et al. |
| 2010/0280325 A1 | 11/2010 | Brahim et al. |
| 2010/0284580 A1 | 11/2010 | OuYang et al. |
| 2010/0286477 A1 | 11/2010 | OuYang et al. |
| 2010/0286782 A1 | 11/2010 | Schaller et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0310352 A1 | 12/2012 | DiMauro et al. |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0190875 A1 | 7/2013 | Shulock et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0310943 A1 | 11/2013 | McCormack et al. |
| 2014/0052259 A1 | 2/2014 | Garner et al. |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257239 A1 | 9/2014 | Arthur et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0277467 A1 | 9/2014 | Hibri et al. |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0230932 A1 | 8/2015 | Schaller |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0045240 A1 | 2/2016 | O'Neil et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0331362 A1 | 11/2016 | O'Neil et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |

(56) References Cited

U.S. PATENT DOCUMENTS

| | | |
|---|---|---|
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0256144 A1 | 9/2018 | O'Neil et al. |

FOREIGN PATENT DOCUMENTS

| | | |
|---|---|---|
| DE | 19710392 C1 | 7/1999 |
| DE | 29916026 U1 | 11/1999 |
| EP | 0 537 116 A1 | 4/1993 |
| EP | 0 807 415 A2 | 11/1997 |
| GB | 2481727 A | 1/2012 |
| WO | 96/29014 A1 | 9/1996 |
| WO | 00/74605 A1 | 12/2000 |
| WO | 2001/056490 A1 | 8/2001 |
| WO | 2001/089371 A1 | 11/2001 |
| WO | 2002/002016 A1 | 1/2002 |
| WO | 2004/103430 A2 | 12/2004 |
| WO | 2008/121162 A1 | 10/2008 |
| WO | 2009/033207 A1 | 3/2009 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/048485, mailed Feb. 9, 2016. (16 pages).
International Search Report and Written Opinion for Application No. PCT/US2015/060978, mailed Feb. 15, 2016 (8 pages).
Invitation to Pay Additional Fees for Application No. PCT/US2016/050022, mailed Nov. 3, 2016 (2 pages).
International Search Report and Written Opinion for Application No. PCT/US2016/050022, issued Feb. 1, 2017 (19 pages).
Prenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
U.S. Appl. No. 11/863,839, filed Sep. 28, 2007, Balloon With Shape Control For Spinal Procedures.
U.S. Appl. No. 14/925,615, filed Oct. 28, 2015, Balloon With Shape Control For Spinal Procedures.
U.S. Appl. No. 15/218,131, filed Jul. 25, 2016, Balloon With Shape Control For Spinal Procedures.
U.S. Appl. No. 15/912,286, filed Mar. 5, 2018, Balloon With Shape Control For Spinal Procedures.

\* cited by examiner

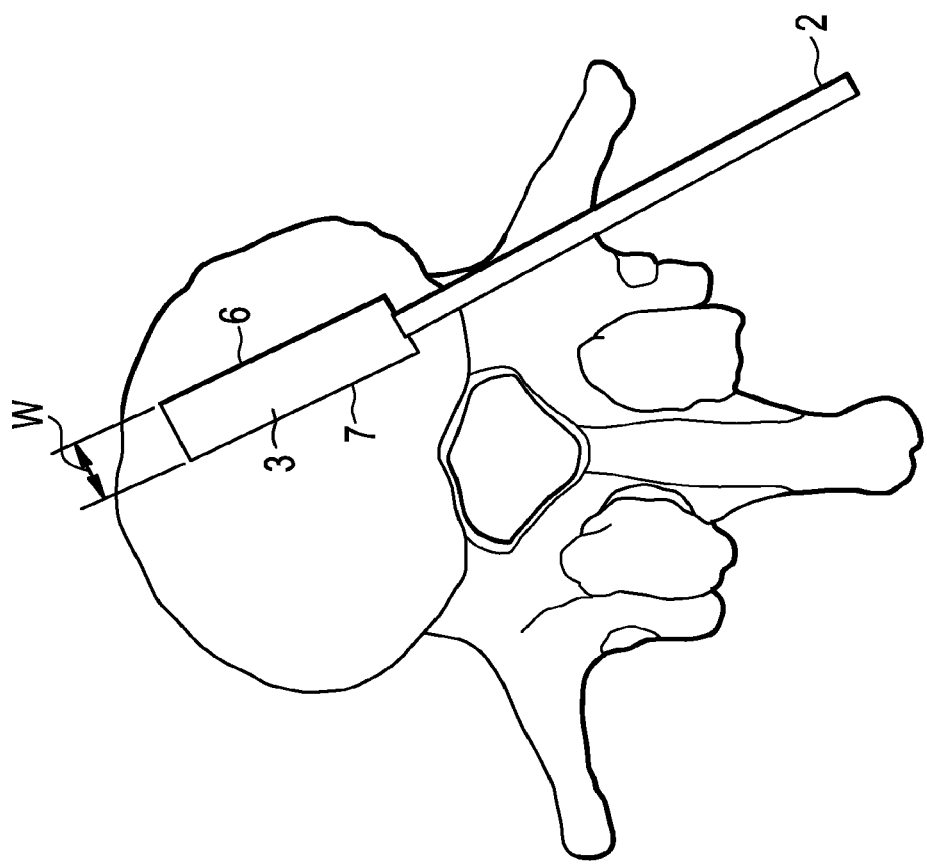
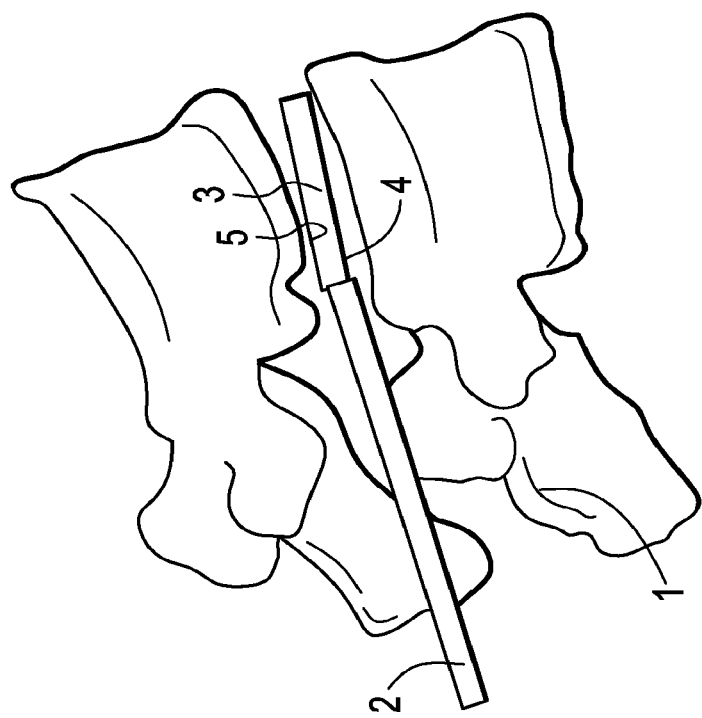
FIG. 1A
FIG. 1B

BALLOON WITH SHAPE CONTROL FOR SPINAL PROCEDURES

CROSS-REFERENCE TO RELATED APPLICATIONS

This application is a continuation of U.S. application Ser. No. 15/912,286, filed Mar. 5, 2018. U.S. patent application Ser. No. 15/912,286 is a continuation of U.S. application Ser. No. 15/218,131, filed Jul. 25, 2016 (now U.S. Pat. No. 9,936,938). U.S. application Ser. No. 15/218,131 is a continuation of U.S. application Ser. No. 14/925,615 filed on Oct. 28, 2015 (now U.S. Pat. No. 9,421,056). U.S. application Ser. No. 14/925,615 is a continuation of U.S. patent application Ser. No. 11/863,839 filed on Sep. 28, 2007 (now abandoned). The entire contents of each of these applications are incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). The cytokines help regulate the metabolism of the nucleus pulposus cells.

In some instances of disc degeneration disease (DDD), gradual degeneration of the intervertebral disc is caused by mechanical instabilities in other portions of the spine. In these instances, increased or unconventional loads and pressures on the nucleus pulposus cause the cells to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins which leads to nerve irritation and pain.

As DDD progresses, the toxic levels of the cytokines present in the nucleus pulposus begin to degrade the extracellular matrix. In particular, the MPPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, and thereby typically upregulating MMPs. As this destructive cascade continues and DDD further progresses, the disc begins to bulge ("a herniated disc"), and then ultimately ruptures, causing the nucleus pulposus to contact the spinal cord and produce pain.

Conventional technology for treating such pain includes the replacing the degenerating disc with either a fusion cage or a motion disc. The literature related to such treatments details the use of both spreader blocks and intra-discal balloons within the intradiscal space. Various spreader blocks are frequently utilized to loosen disc tissue, expand/regain disc height, and encourage vertebral body endplate vascularity. General in-situ balloon art also includes stand alone implants and balloons reinforced with bands, fabrics or scaffolds to enable directional growth.

U.S. Pat. No. 6,632,235 (Weikel) discloses a balloon for insertion into the disk space and inflated to distract the vertebrae. The controlled inflation of the balloon may ensure optimum distraction of the vertebrae and facilitate maximum implant height and neural foraminal decompression. If the balloon is to serve as a distraction instrument, a bone or synthetic allograft along with cancellous bone graft or filler material may then be implanted into contralateral disc space. Once the implant and other materials are in the desired position, the balloon may be deflated and removed from the disk space and a second implant of the same height may be inserted into that space. If the balloon is to serve as a spacer for intervertebral body fusion, the balloon may be inflated with a filler material that sets to form an synthetic allograft implant in vivo. Once the implant has been adequately formed, the balloon may be lysed and removed from the disk space. In another example, the inflated balloon is left intact and is separated from the catheter to remain within the disk space as a scaffold for new bone growth. As previously described, a balloon implant also may be resorbed by physiological conditions and expelled from the patient or transformed and remodeled into new bone growth.

U.S. Pat. No. 6,332,894 (Stalcup) discloses an orthopaedic implant for implanting between adjacent vertebrae and a spine, includes a generally annular bag; and a hardened polymer with the bag. The method of fusing adjacent vertebrae in a spine includes the steps of forming an access hole in an annulus of a disc between the adjacent vertebrae; removing the nucleus within the disc to form a cavity surrounded by the annulus; placing a generally annular bag within the cavity; filling the bag with a polymer; injecting bone particles into the cavity surrounded by the annular bag; and hardening the polymer.

US Published Patent Application 2006/0264945 (Edidin) discloses a scaffold configured to be disposed in a bone. The scaffold is configured to move from a first configuration to a second configuration. The scaffold in the second configuration is expanded from the first configuration. A selectively-expandable actuator is configured to be removably disposed within the scaffold. The selectively-expandable actuator is configured to move at least a portion of the scaffold to the second configuration when the selectively-expandable actuator is moved to an expanded configuration. A shape of the selectively-expandable actuator is substantially the same as a shape of the scaffold when the selectively-expandable actuator and the scaffold are in the second configuration. The selectively-expandable actuator configured to be removed from the scaffold when in a collapsed configuration. The scaffold is configured to remain substantially in the second configuration after the scaffold has been expanded by the actuator.

US Published Patent Application US2005/0070900 (Serhan) discloses an intervertebral fusion device includes a body having a proximal portion along a major axis of the body and a distal portion along the major axis, and supporting means at the distal portion. The supporting means supports vertebrae in a distracted position while the vertebrae fuse. At least one of the body and the supporting means has a height distinct from a width, whereby the body or supporting means can distract vertebrae, between which the body or the supporting means has been placed, by rotation of the body or the supporting means about the major axis. A method of fusing vertebrae includes the steps of inserting between two vertebrae an intervertebral fusion device and rotating the body or the supporting means, whereby the vertebrae are supported in a distracted position while the vertebrae fuse. US2004/0073213 (Serhan) discloses a device for distracting two vertebral bodies and delivering a flowable material into the disc space, comprising a body having a proximal portion and a distal portion, the distal portion having a shape adapted to distract, the body also having a longitudinal bore defining a first outlet port in the distal portion, and a first injection port in the proximal portion.

US Published patent applications US2005/0070900 and US2004/0073213 disclose fluid dispensing through a spreader block. These applications require the balloon(s) to be in direct fluid communication with the spreader.

SUMMARY OF THE INVENTION

The general concept of the present invention relates to devices and methods for minimally invasive disc space distraction and implantation to address degenerative disc disease (DDD), HNP, stenosis, or other conditions of a functional spinal unit.

This present invention uses separate or pre-attached spreader blocks to control the directional growth of the distracting balloon. Preferably, fluid communication to the balloon is not achieved through the block. In addition, spreader block material, geometry and surgical placement options are disclosed to ensure directional expansion including vertical growth for increasing disc space height.

Spreader blocks and a balloon of the present invention are used together as either disc distraction instruments and/or implants. Spreader blocks of varying sizes and shapes are employed to contain balloon expansion in various planes. The balloon containment embodiments that are disclosed herein assist in ensuring directional expansion to accomplish vertical growth for increasing disc space height. The various combinations of balloon and spreader blocks concepts can be divided into (a) non-attached and (b) pre-attached or conjoined embodiments.

Unattached Spreader Blocks and Balloons:

In some embodiments, the spreader blocks and balloon are not physically joined together and so are independent.

Single Spreader Block (See FIGS. 1a-3b).

In one example thereof, a single spreader block and a single independent balloon are initially placed within the disc space. The spreader block is rotated to loosen the annulus fibrosus and regain some of the collapsed disc height. The balloon is then inflated, thereby filling the cleared disc cavity defined by the spreader block and the natural annulus and further distracting the disc to regain even more disc height. The spreader block both limits radial expansion of the balloon and thereby encourages vertical balloon expansion.

Multiple Spreader Blocks:

In other examples wherein the spreader blocks and balloon are independent (i.e., not physically joined together), multiple spreader blocks can be employed to control balloon expansion in multiple directions. See FIGS. 4a-6b. Various spreader block geometries can be used to control balloon expansion towards desired directions or into desired locations. For example, in some embodiments (FIGS. 7a-10b), a curved spreader (which is not rotated) is employed to direct balloon expansion away from the anterior and lateral portions of the annulus fibrosus. In other embodiments (FIGS. 11a & 12b), a slotted spreader block directs balloon expansion to a relatively narrow vertical support beam, thereby significantly limiting balloon expansion in the axial plane and enabling increased balloon expansion in the cranial/caudal plane.

Shape Memory Spreader:

In some embodiments, a shape memory insert is provided as a means for containing the expansion of the balloon in the radial plane while allowing free expansion in the cephalad-caudal directions. See FIGS. 13a-f. The shape memory insert can create a curved barrier, or it can lock upon itself, thereby forming a full ring as the sleeve is retracted (or the shape memory insert advanced). In other embodiments, the shape memory insert may be left free to act as a spring allowing some expansion of the balloon in the coronal/saggital plane.

In some shape memory embodiments, there is provided a method of using a shape memory balloon containment instrument in a disc space, comprising the steps of:

a) inserting an instrument comprising an insert and a sleeve into disc space,
b) moving the sleeve relative to the insert to expose the insert, and thereby allowing the insert to curve, contact, connect and/or lock upon itself,
c) inserting a cannula and a balloon contained therein through a guide channel in the insert,
d) expanding the balloon,
e) retracting the insert through the sleeve, and
f) removing the sleeve while allowing the expanded balloon to remain behind.

Integrated Spreaders and Balloons:

In another embodiment, the spreader block may further possess a means of balloon delivery and expansion. In this case, the balloon and spreader block(s) are provided in an integrated (attached) state and inserted into the disc space as an assembly. Such integrated assemblies can be adapted to carry out to several of the previous concepts. For instance, the spreader block can have a pocket or recess to contain the balloon (see FIGS. 14a-b and 15a-b). Alternatively (as seen in FIG. 16a-19b), the spreader block functions as an inserter/spacer to enable balloon expansion and a combination of spreader and balloon geometry controls direction of balloon expansion. In these integrated embodiments, after its expansion, the balloon can be disconnected from the spreader with which it is integrated by cutting or twisting, typically at predetermined break-off locations.

In an alternative embodiment, the balloon is contained within a sectioned spreader block. The spreader block is inserted into a cleared, collapsed disc space, and rotated to regain disc height. Then the balloon is filled. As the balloon fills, it deploys outwards from the spreader block. Sections of the spreader block that are temporarily attached to the balloon deploy with the balloon. The function of these deployed sections is to control the expansion of the balloon—if the deployable spreader block sections are hinged to the base of the spreader block, they only allow the balloon to deploy into an arcuate shape (as depicted in FIGS. 20a-21b. Also, the deployed spreader block sections could help prevent the expanding balloon from assuming a circular cross-section, thereby achieving a long, tall, arcuate balloon (rather than a curved hot dog shape). In these embodiments, the balloon could be operated under high pressure (to cause additional disc space distraction) or low pressure (requiring the spreader block to perform the mechanical work). In this alternative embodiment, the final implant would be the filled, cured, deployed balloon strut in a generally arcuate shape.

In another alternative embodiment, the device includes joined balloon ends with a filler mechanism in the middle. Upon filling, this balloon would assume a crescent shape with the narrow ends of the crescent being attached by a "tether" of unfilled balloon material. This embodiment would provide an arcuate, filled balloon but constructed from multiple circular devices. Thus, a high-pressure balloon is constructed that deploys through a spreader block, distracts the disc space, and forms a self-stable implant strut.

In both the independent and intergrated balloon/spreader embodiments, the balloon can be used as an instrument or as an implant. When utilized as an instrument, the balloon is filled with a fluid (such as a gas, liquid or semi-solid (saline, contrast agent, radiopaque gel, etc.) to confirm the disc space cavity volume via monitoring the injectate volume and shape via intra-operative imaging. In some embodiments, the injectate can then be evacuated from the balloon and an implant inserted in the disc space. In others, the same balloon (or a new balloon) can be filled with an implant-grade material that encourages fusion (bone cements, osteoinductive cements, bone particles, bone substitutes, growth factors, BMP, etc. . . . ) or maintains motion (viscous gels, cureable elastomers, hydrogels, etc. . . . ).

DESCRIPTION OF THE FIGURES

FIGS. 1a-3b disclose the use of a single spreader block and balloon within the disc space.

DETAILED DESCRIPTION OF THE INVENTION

Figure 2A:
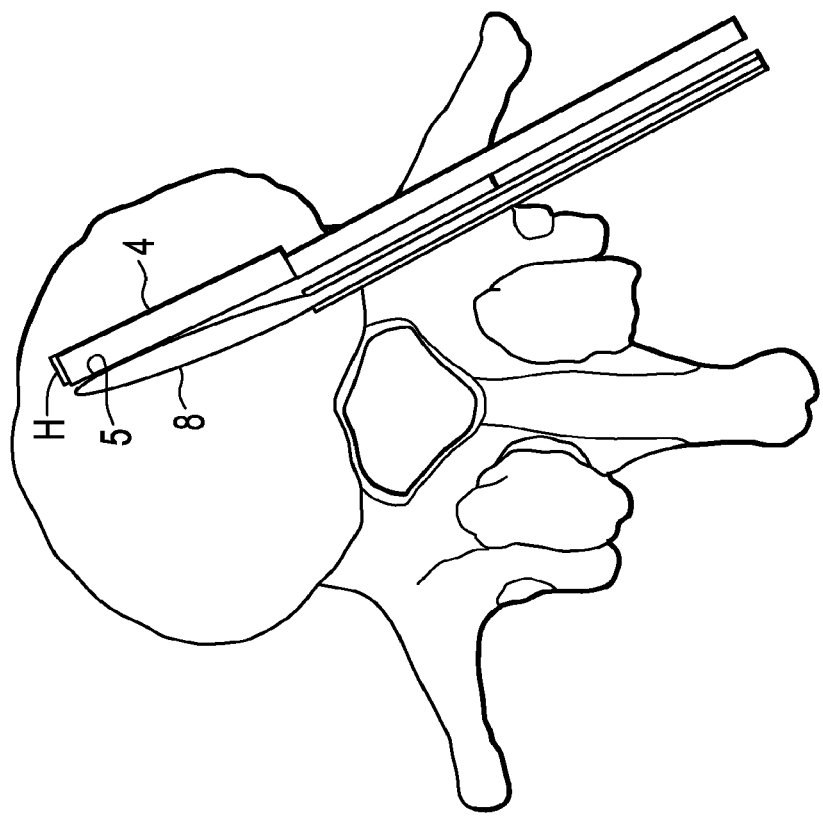
Figure 2B:
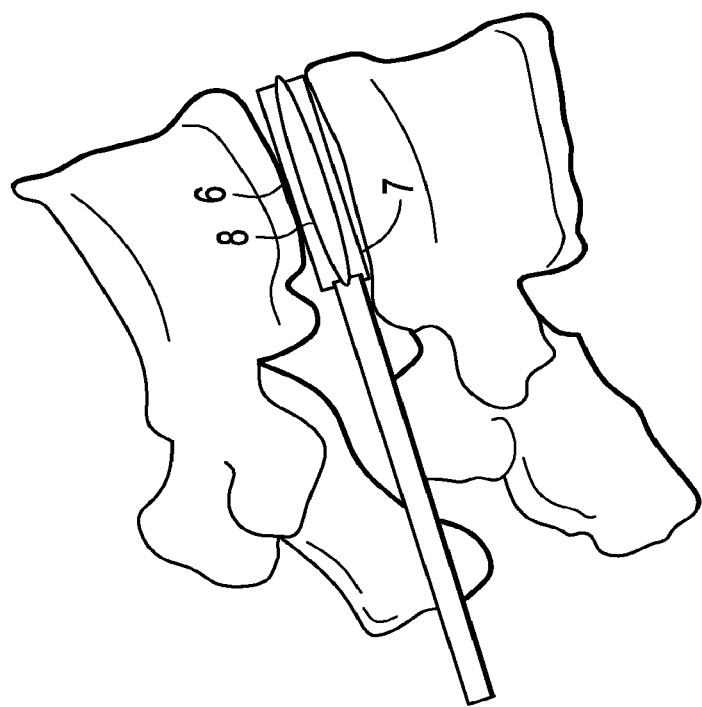
Figure 3B:
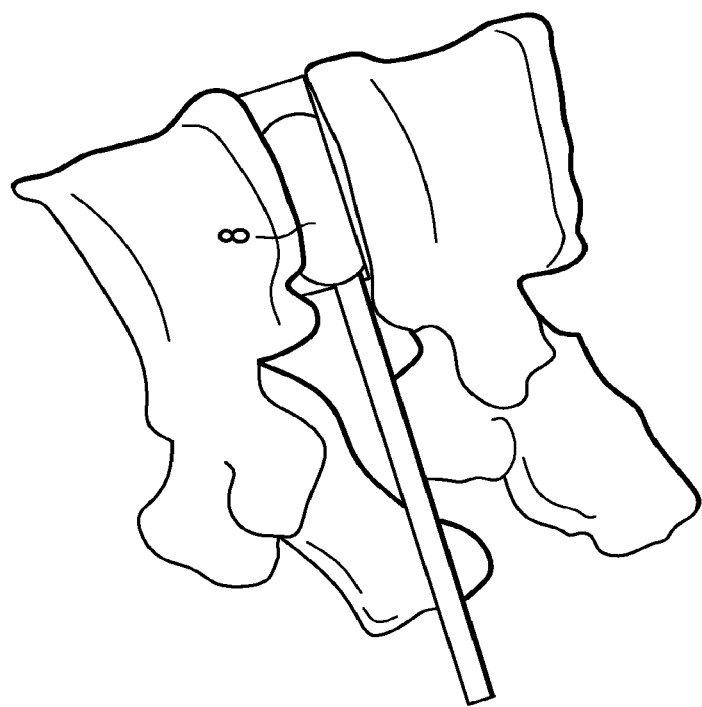
Figure 3A:
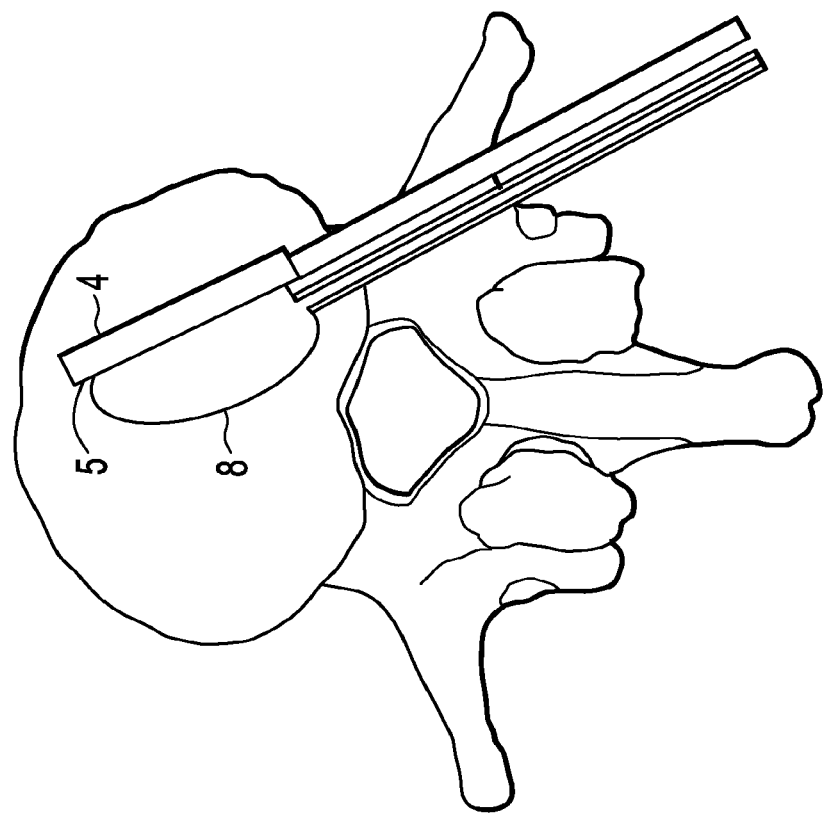
Figure 4B:
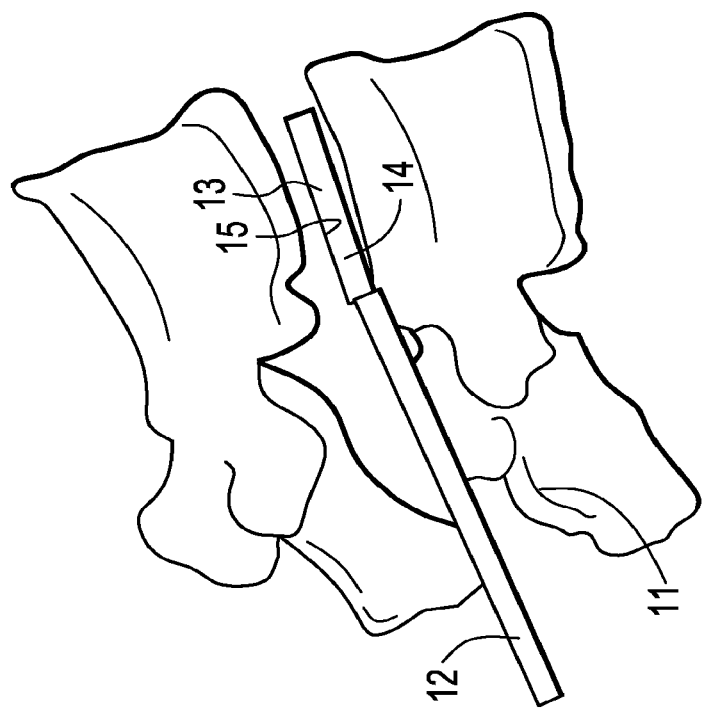
FIGS. 4a-6b disclose the use of two spreader blocks and a balloon within the disc space to limit radial expansion of the balloon.
Figure 4A:
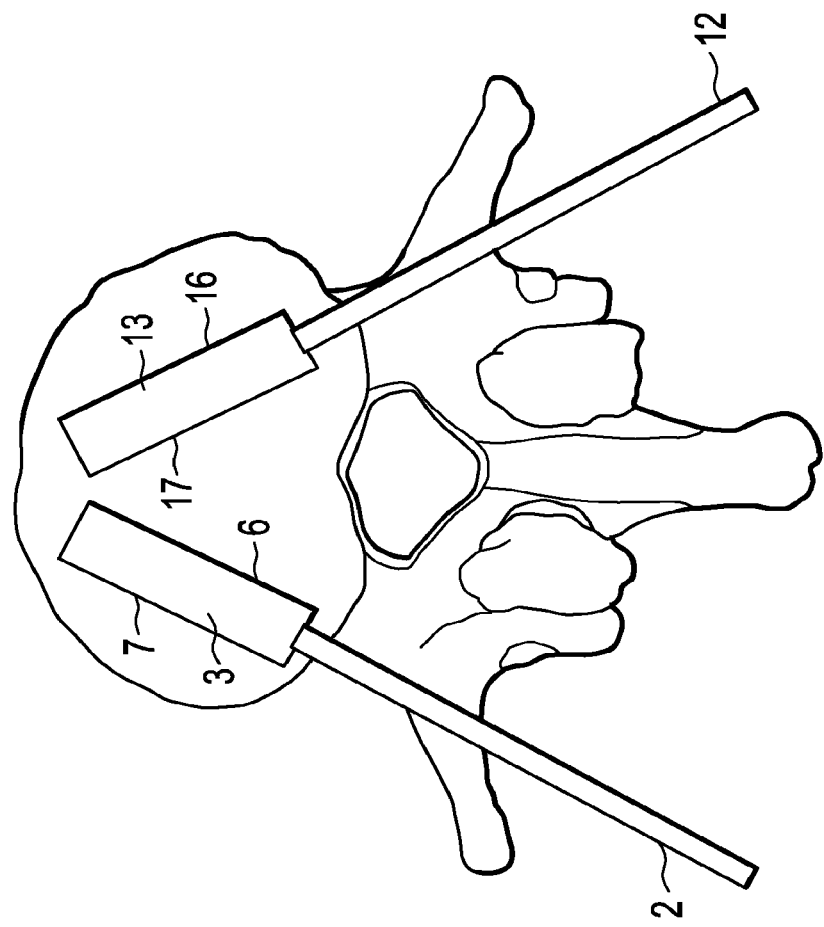
Figure 5B:
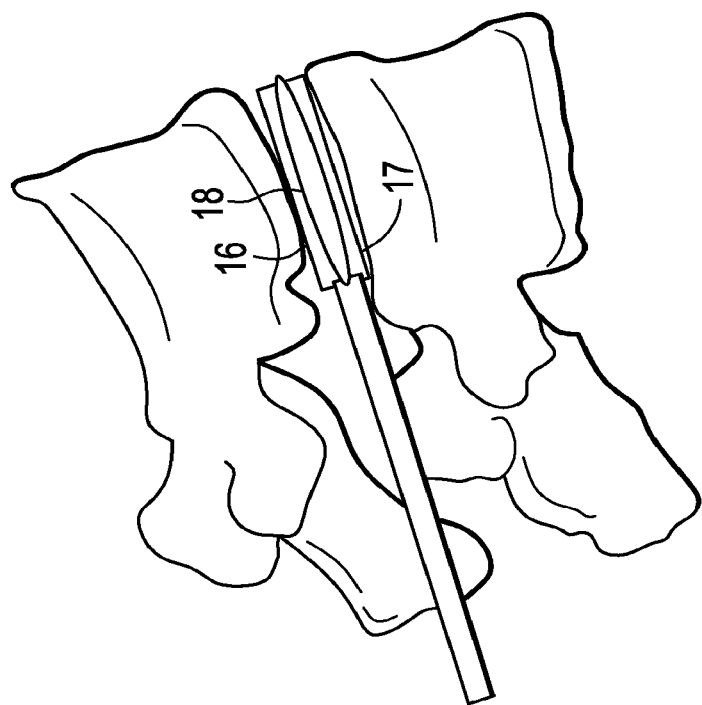
Figure 5A:
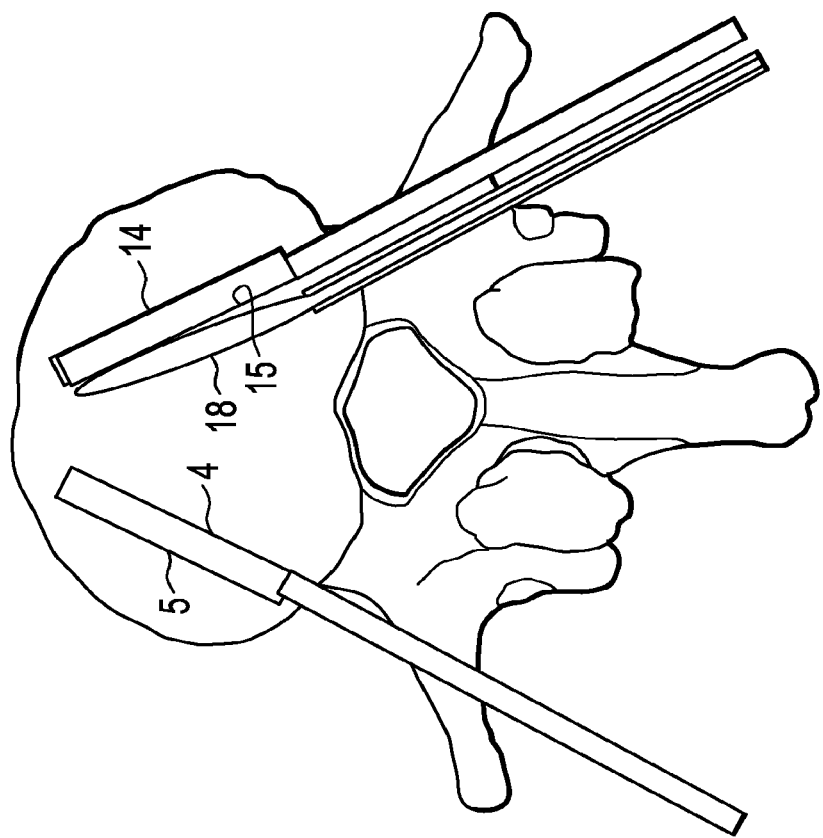
Figure 6B:
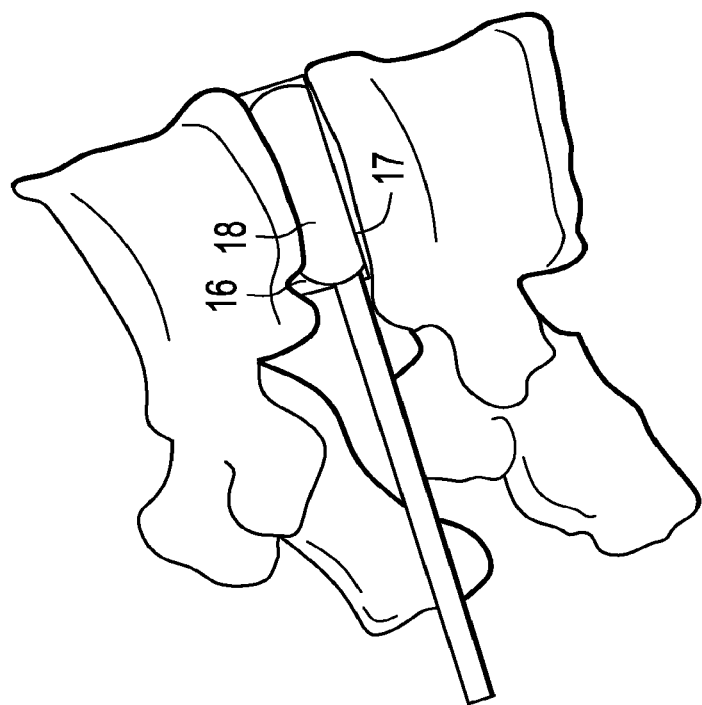
Figure 6A:
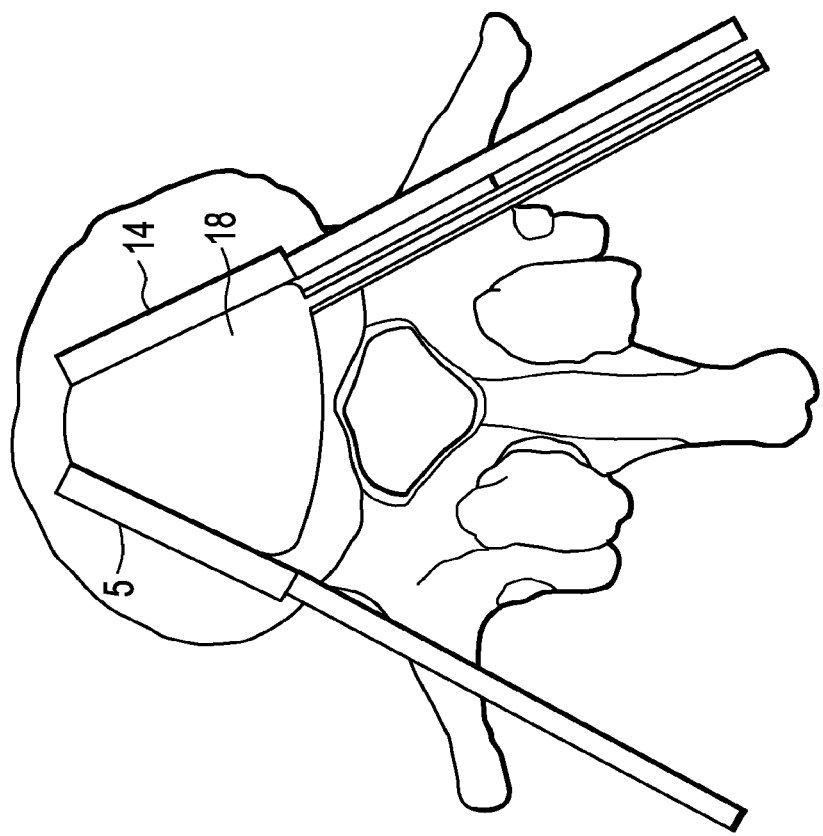
Figure 7B:
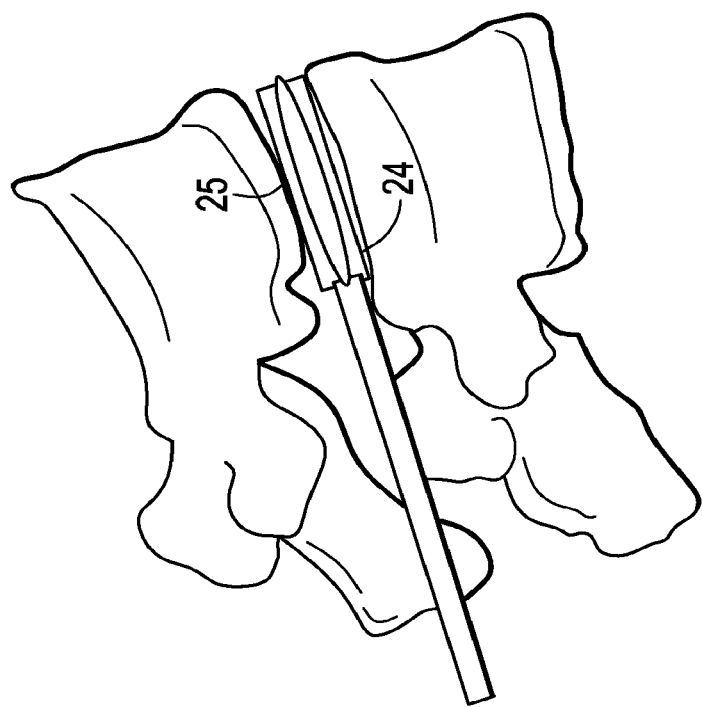
FIGS. 7a-8b disclose the use of a single curved spreader block and balloon within the disc space.
Figure 7A:
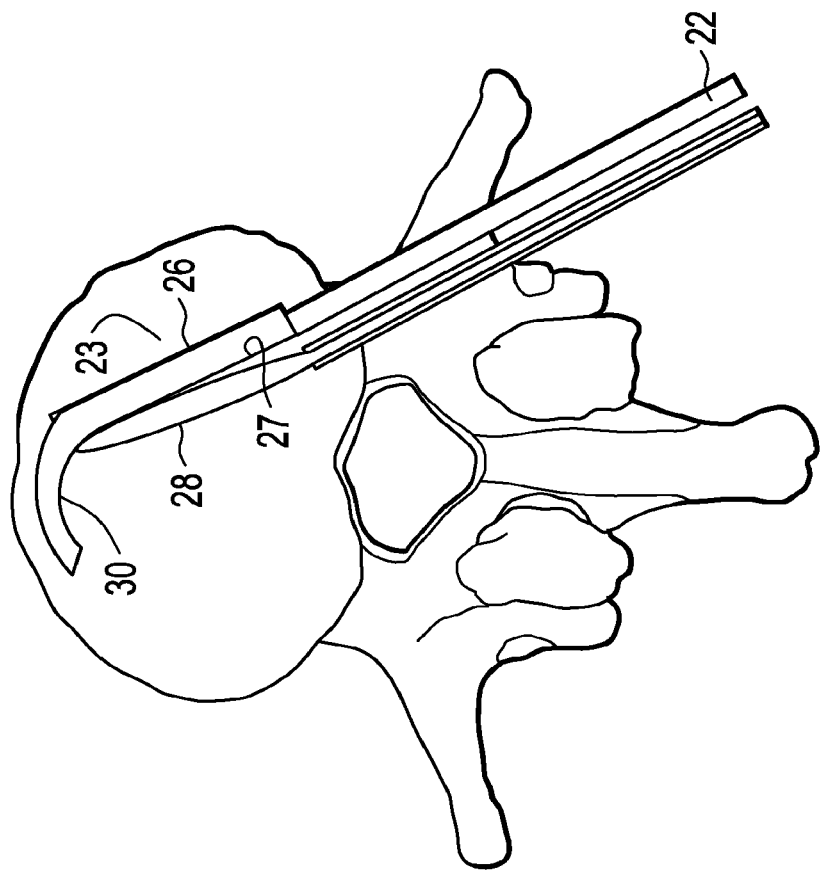
Figure 8B:
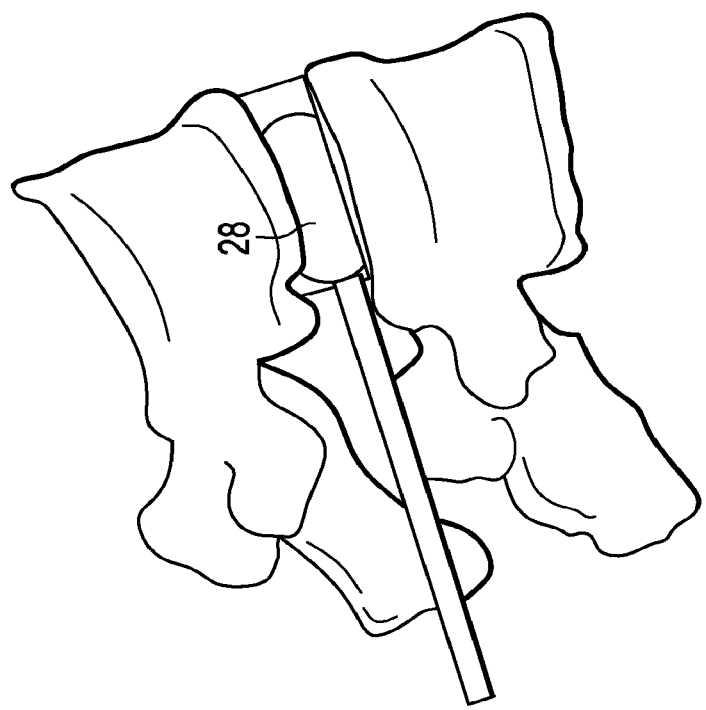
Figure 8A:
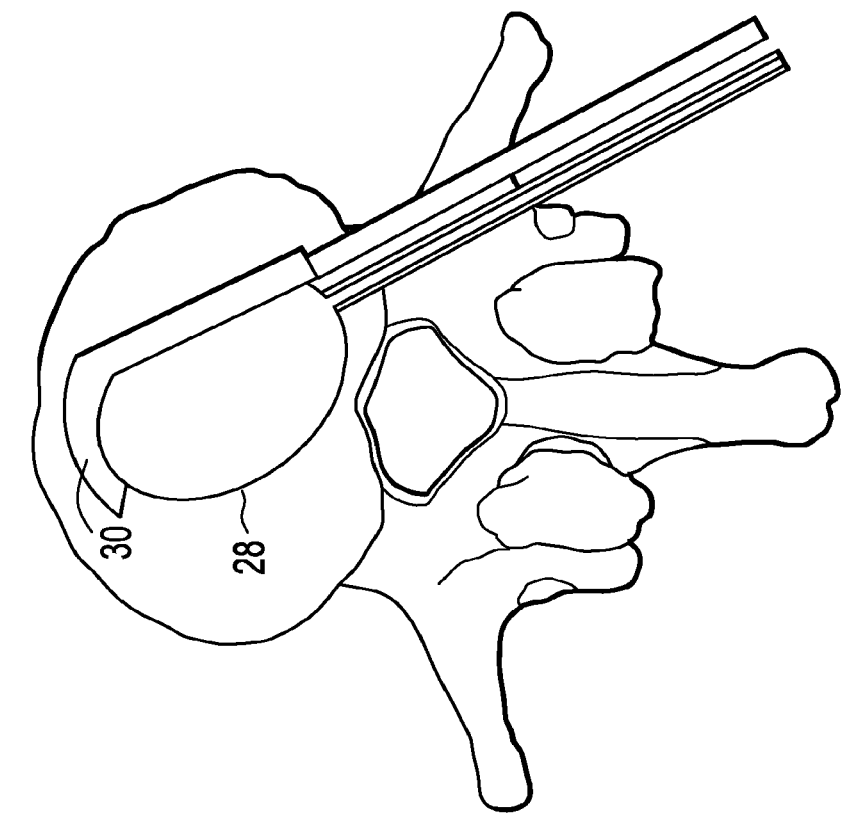
Figure 9B:
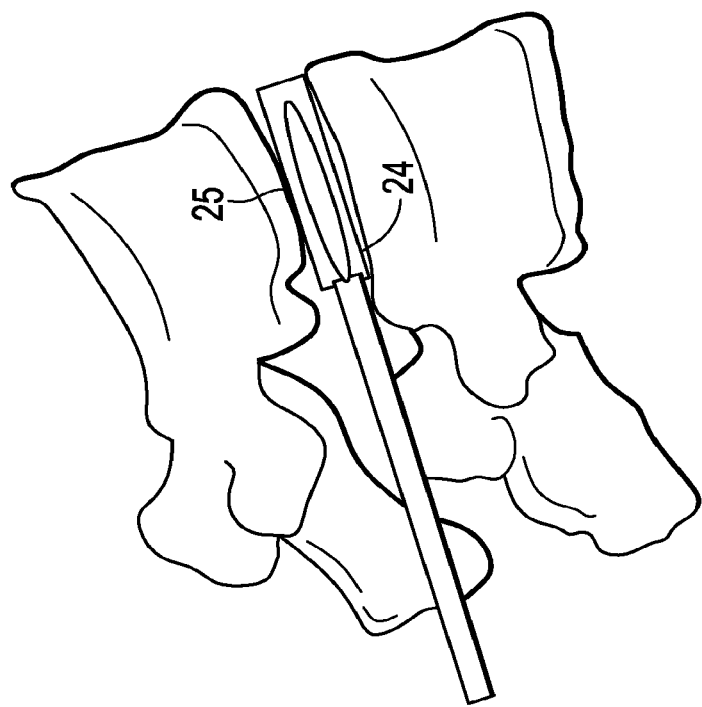
FIGS. 9a-10b disclose the use of a curved spreader block, a straight spreader block and a balloon within the disc space to limit radial expansion of the balloon.
Figure 9A:
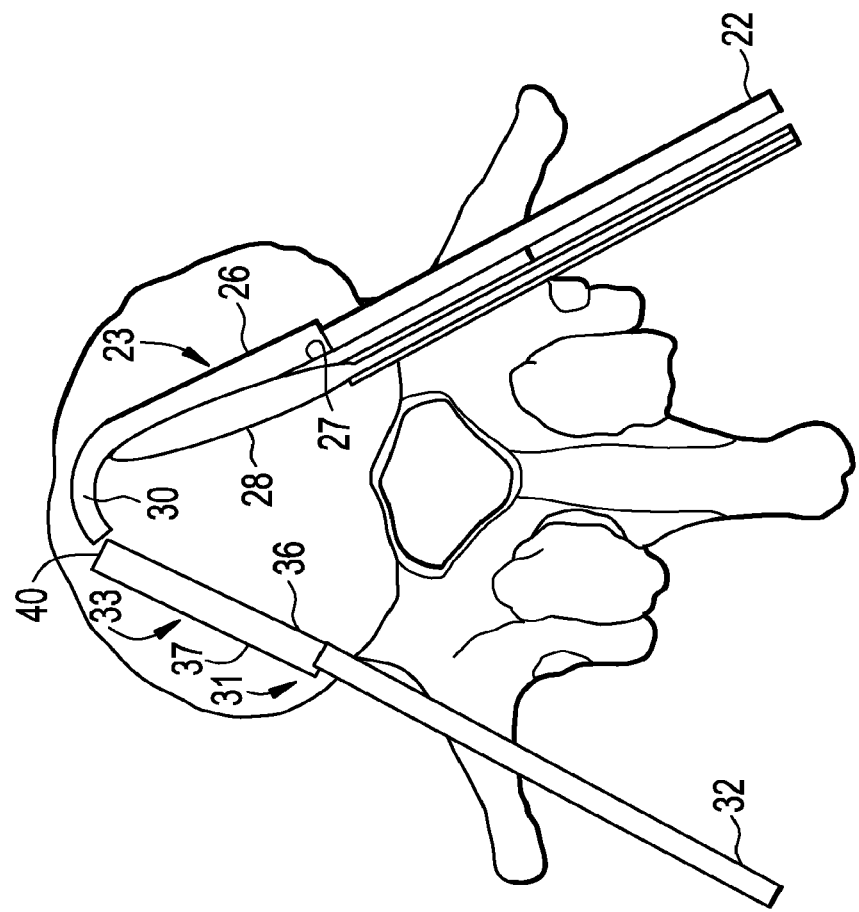
Figure 10B:
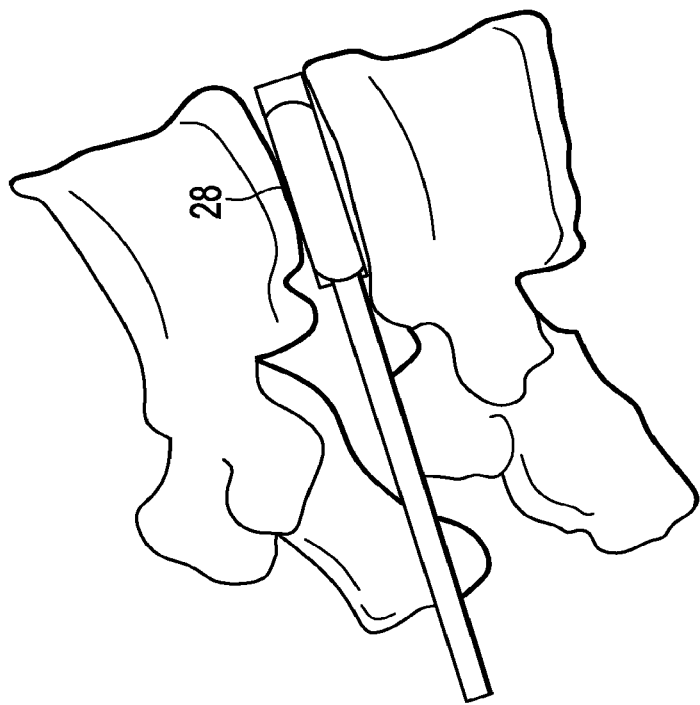
Figure 10A:
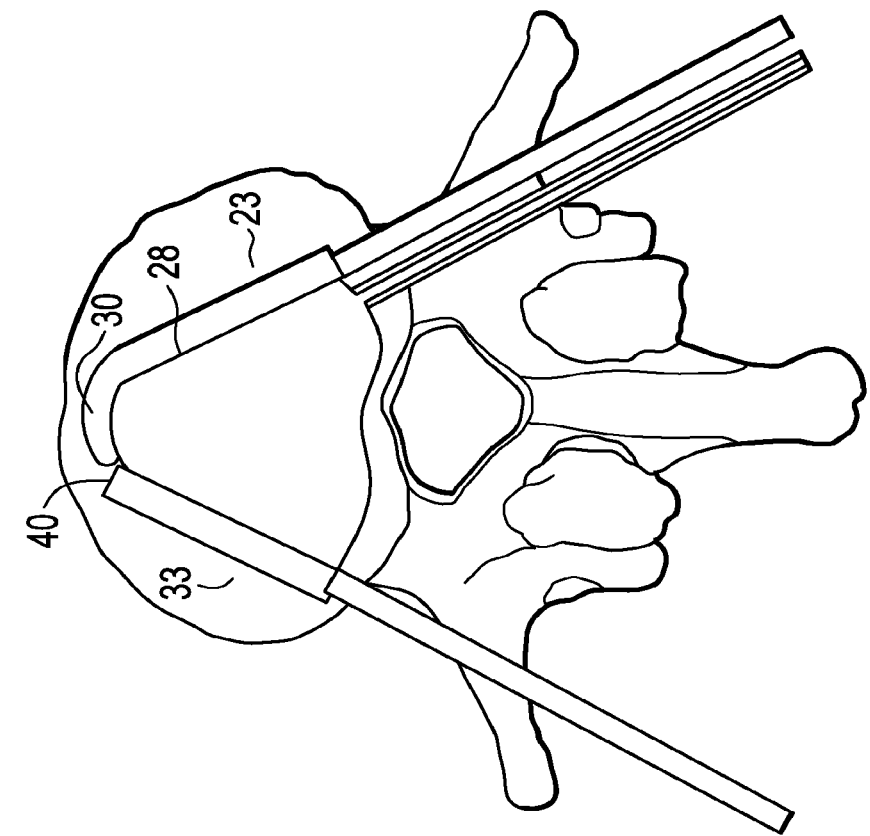
Figure 11B:
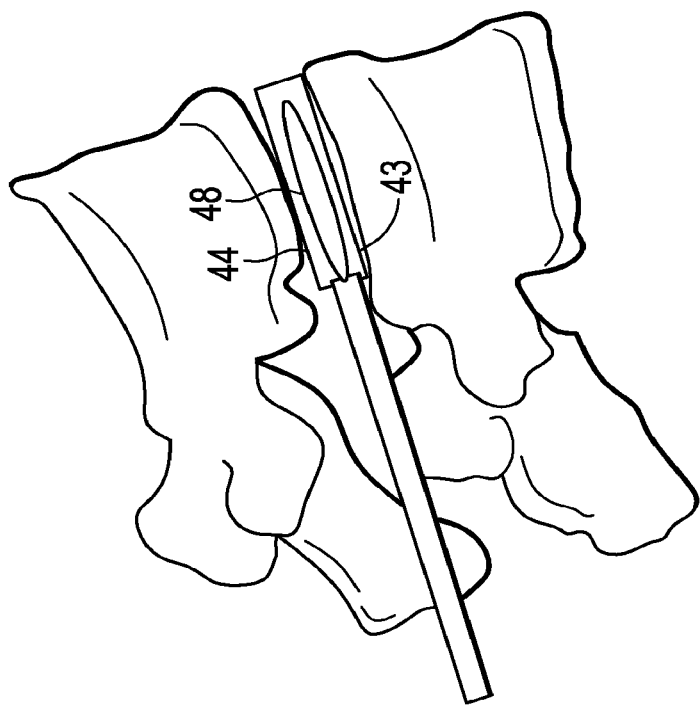
FIGS. 11a-12b disclose the use of a single slotted spreader block and balloon within the disc space.
Figure 11A:
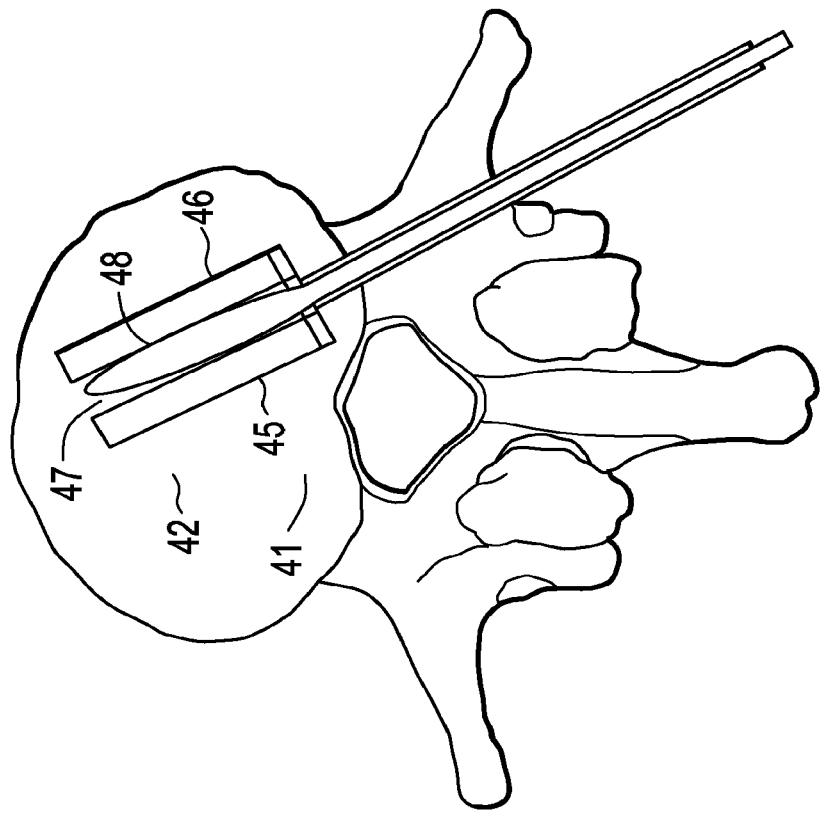
Figure 12B:
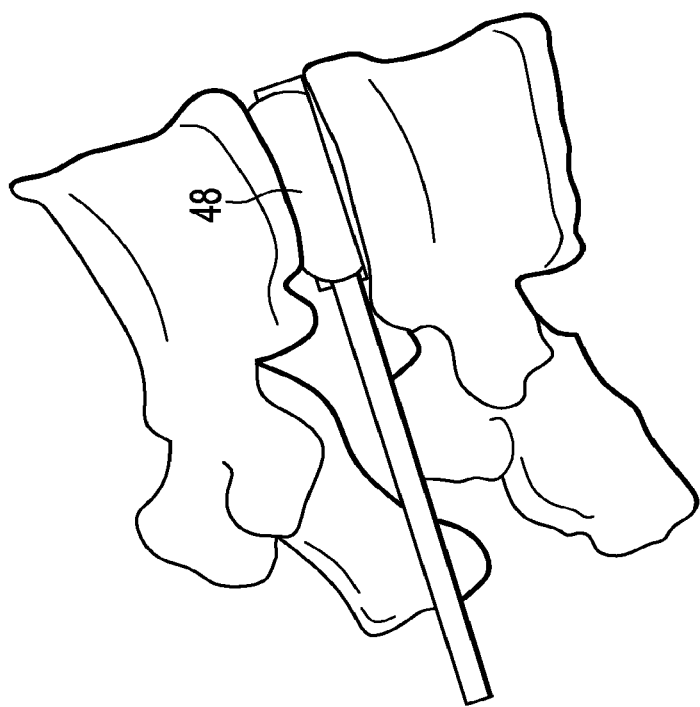
Figure 12A:
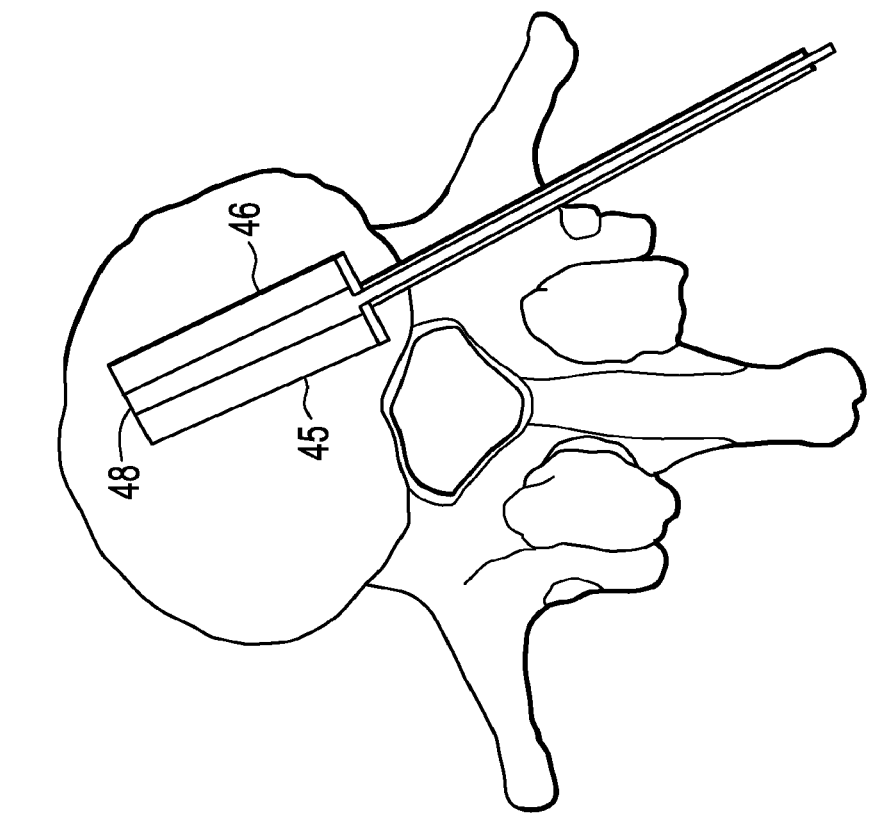
Figure 13C:
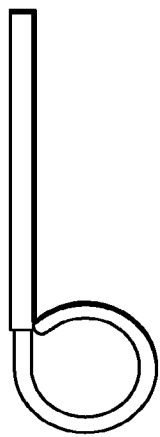
FIG. 13a-f discloses an embodiment utilizing a shape memory structure.
Figure 13B:
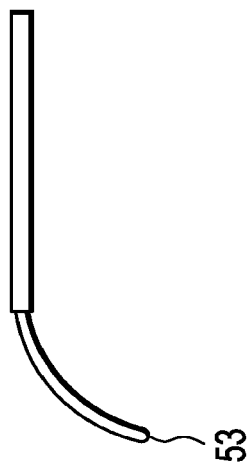
Figure 13A:
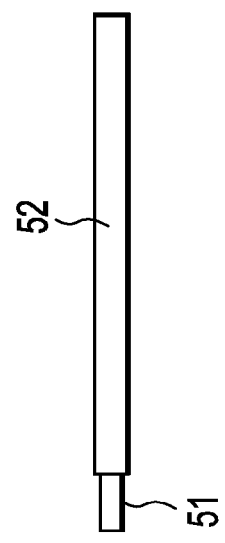
Figure 13F:
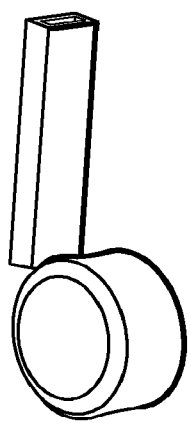
Figure 13E:
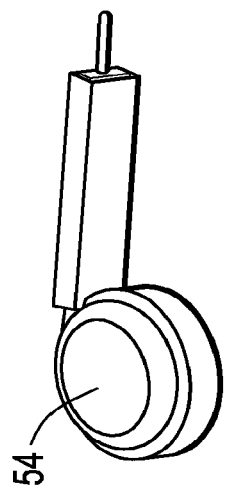
Figure 13D:
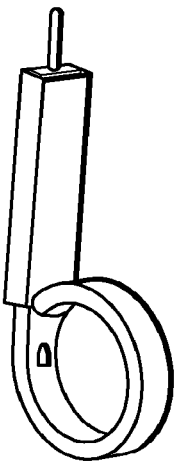

Generally, in independent (or "unattached") embodiments, there is generally provided:
a) a spreader insertion instrument comprising a proximal handle and a distal spreader block having a distal end portion, a height defined by first and second surfaces, and a width defined by third and fourth surfaces, and
b) an inflatable device comprising i) a proximal cannula having a proximal end and a distal end, and ii) a distal balloon having a proximal opening attached to the distal end of the cannula.

A first function of the spreader insertion instrument is to provide an initial distraction of the disc space. Typically, the width of the spreader block is greater than its height (i.e., the distance between its third and fourth surfaces exceeds the distance between its first and second surfaces). Accordingly, when the spreader block is inserted into the disc space (so that its first and second surfaces contact the endplates) and then rotated 90 degrees (so that its third and fourth surfaces contact the natural endplates), the distance between the endplates is increased and distraction is achieved.

The primary function of the balloon is to achieve a further distraction of the disc space. This is accomplished by inserting the balloon into the disc space and inflating the balloon. The inflated balloon pushes against the opposed endplates and enables distraction of the disc space. However, because many conventional balloons are not equipped with a directional bias, the typical balloon expands according to its path of least resistance. Since the opposing endplates present significant resistance to balloon expansion, conventional balloon expansion occurs substantially in the radial direction, that is, parallel to the endplates, thereby lessening its potential to desirably distract of the disc space.

Therefore, a second function of the spreader is to constrain the directional expansion of the balloon. Simply, the spreader provides a blocking function that prevents too much radial expansion of the balloon and directs expansion to occur in the vertical direction, which provides the desired distraction.

In one embodiment of the present invention, and now referring to FIGS. 1a-3b, there is provided a method of treating a disc, comprising the steps of:
a) providing an insertion instrument 1 comprising a proximal handle 2 and a distal rotatable spreader block 3 having a height H defined by first 4 and second 5 surfaces and a width W defined by third 6 and fourth 7 surfaces,
b) inserting the spreader block into the disc space so that the first and second surfaces thereof contact the opposed vertebral body endplates,
c) rotating the spreader block in the disc space so that the third and fourth surfaces thereof contact the opposed vertebral body endplates,
d) inserting an uninflated balloon 8 into the disc space adjacent the spreader block,
e) inflating the balloon so that the balloon contacts one of the first and second surfaces of the spreader block.

The method disclosed in FIGS. 1a-3b allows the surgeon to sequentially achieve the desired distraction by using an independent balloon and spreader block. The block directs expansion of the balloon in a preferred direction. When the desired distraction is achieved, an intervertebral implant may be inserted into the distracted disc space. After the implant is firmly implanted, the balloon and spreader block may be removed.

In another embodiment of the present invention, and now referring to FIGS. 4a-6b, there is provided a method of treating a disc, comprising the steps of:
a) providing first 1 and second 11 insertion instruments, each instrument comprising a proximal handle 2,12 and a distal rotatable spreader blocks 3,13, each block having a height defined by first 4,14 and second 5,15 surfaces and a width defined by third 6,16 and fourth 7,17 surfaces,
b) inserting each spreader block into the disc space so that the first and second surfaces thereof contact the opposed vertebral body endplates, c) rotating each spreader block in the disc space so that the third and fourth surfaces thereof contact the opposed vertebral body endplates,
d) inserting an uninflated balloon 18 into the disc space between the spreader blocks,
e) inflating the balloon so that the balloon contacts one of the first and second surfaces of each spreader block.

The method disclosed in FIGS. 4*a*-6*b* allows the surgeon to sequentially achieve the desired distraction using an independent balloon and two spreader blocks, wherein the inner surfaces of the opposed spreader blocks define the extremities of radial expansion of the balloon. Thus, the surgeon can control a substantial portion of the footprint made by the balloon in the disc space through the use of a pair of spreader blocks.

In another embodiment of the present invention, and now referring to FIGS. 7*a*-8*b*, there is provided a method of treating a disc, comprising the steps of:
a) providing an insertion instrument 21 comprising a proximal handle 22 and a distal spreader block 23 having a curved distal end portion 30, a height defined by first 24 and second 25 surfaces and a width defined by third 26 and fourth 27 surfaces,
b) inserting the spreader block into the disc space so that the first and second surfaces thereof contact the opposed vertebral body endplates,
c) inserting an uninflated balloon 28 into the disc space adjacent the spreader block,
d) inflating the balloon so that the balloon contacts the distal end portion of one of the first and second surfaces of the spreader block.

The method disclosed in FIGS. 7*a*-8*b* is similar to that of FIGS. 1*a*-3*b* in that each allows the surgeon to sequentially achieve the desired distraction using an independent balloon and spreader block. However, in FIGS. 7*a*-8*b*, the distal end of the spreader block is curved, thereby constraining the radial expansion of the spreader block.

In another embodiment of the present invention, and now referring to FIGS. 9*a*-10*b*, there is provided a method of treating a disc, comprising the steps of:
a) providing a first insertion instrument 21 comprising a proximal handle 22 and a distal spreader block 23 having a curved distal end portion 30, a height defined by first 24 and second 25 surfaces and a width defined by third 26 and fourth 27 surfaces,
b) providing a second insertion instrument 31 comprising a proximal handle 32 and a distal spreader block 33 having a distal end portion 40, a height defined by first and second surfaces and a width defined by third 36 and fourth 37 surfaces,
c) inserting each spreader block into the disc space so that the distal end portions are substantially in contact, and the first and second surfaces thereof contact the opposed vertebral body endplates,
d) inserting an uninflated balloon 28 into the disc space between the spreader blocks,
e) inflating the balloon so that the balloon contacts the distal end portion of each spreader block.

The method disclosed in FIGS. 9*a*-10*b* is similar to that of FIGS. 4*a*-6*b* in that each allows the surgeon to sequentially achieve the desired distraction using an independent balloon and two spreader blocks. It is also similar to that of FIGS. 7*a*-8*b*, in that the distal end of one spreader block is curved, thereby constraining the radial expansion of the spreader block. Therefore, in this embodiment, the surgeon can control an even greater portion of the footprint made by the balloon in the disc space through the use of a pair of spreader blocks.

In another embodiment of the present invention, and now referring to FIGS. 11*a*-12*b*, there is provided a method of treating a disc, comprising the steps of:
a) providing an insertion device 41 comprising i) a spreader block 42 having a height defined by first 43 and second 44 surfaces, a width defined by third 45 and fourth 46 surfaces, and a slot 47 extending between the first and second surfaces, and ii) an uninflated balloon 48 within the slot;
b) inserting the spreader block into the disc space so that the first and second surfaces thereof contact the opposed vertebral body endplates, and
c) inflating the balloon so that the balloon substantially contacts one of the first and second surfaces of each spreader block.

In this embodiment, the spreader block has a through-slot extending in the vertical direction. The block is inserted into the disc space so that the slot contacts the opposing endplates. Expansion of the balloon occurs through the slot and so occurs substantially in the vertical direction, thereby forcing the endplates apart and creating distraction.

In another embodiment of the present invention, and now referring to FIGS. 13*a*-13*f*, there is provided a method of treating a disc, comprising the steps of:
a) providing a pair of co-axial outer 51 and inner 52 cannulae, wherein the inner cannula has a distal portion 53 comprising a delivery hole and comprises a shape memory material,
b) inserting the co-axial outer and inner cannulae into the disc space,
c) moving the outer cannula relative to the inner cannula to expose the inner cannula (for example, retracting the outer cannula), thereby causing the distal portion of the inner shape memory cannula to revert to a memorized annular shape having an inner surface including the delivery hole,
d) delivering an uninflated balloon 54 to the disc space through the delivery hole of the inner cannula, and
e) inflating the balloon to substantially contact the inner surface of the memorized annular shape, and
f) retracting the inner cannula.

In this embodiment, a shape memory insert is provided as a means for containing the expansion of the balloon in the radial plane while allowing free expansion in the cephalad-caudal directions. Once, the balloon shape has been created within the shape memory structure, the balloon may be filled with a curable substance that fixes the shape of the balloon. The shape memory structure may then be withdrawn.

In another embodiment of the present invention, and now referring to FIGS. 14*a*-15*b*, there is provided a method of treating a disc, comprising the steps of:
a) providing an distractor comprising:
i) a proximal cannulated handle 61 having a through-bore, and
ii) a distal portion 70 attached to the handle comprising a rotatable spreader block 62 having a height defined by first 63 and second 64 surfaces and a width defined by third 65 and fourth 66 surfaces, and an uninflated balloon 68 having an open end 69 attached to the throughbore and adjacent one of the first and second surfaces of the spreader block,
b) inserting the distractor into the disc space so that the first and second surfaces thereof contact the opposed vertebral body endplates, c) rotating the spreader block in the disc space so that the third and fourth surfaces thereof contact the opposed vertebral body endplates,
d) inflating the balloon so that the balloon contacts the opposed vertebral body endplates and is directionally biased by one of the first and second surfaces of the spreader block This method provides for use of an integrated distractor, wherein the balloon and spreader are attached.

Also in accordance with the present invention, and still referring to FIGS. 14a-15b, there is provided a distractor comprising:
  i) a proximal cannulated handle having a throughbore, and
  ii) a distal portion attached to the handle comprising:
    a rotatable spreader block having a height defined by first and second surfaces and a width defined by third and fourth surfaces, and
    an uninflated balloon having an open end attached to the throughbore.

In some embodiments, the one of the first and second surfaces of the spreader block is recessed to form a pocket in which the uninflated balloon resides. The pocket protects the uninflated balloon during its insertion into the disc space.

Figure 14B:
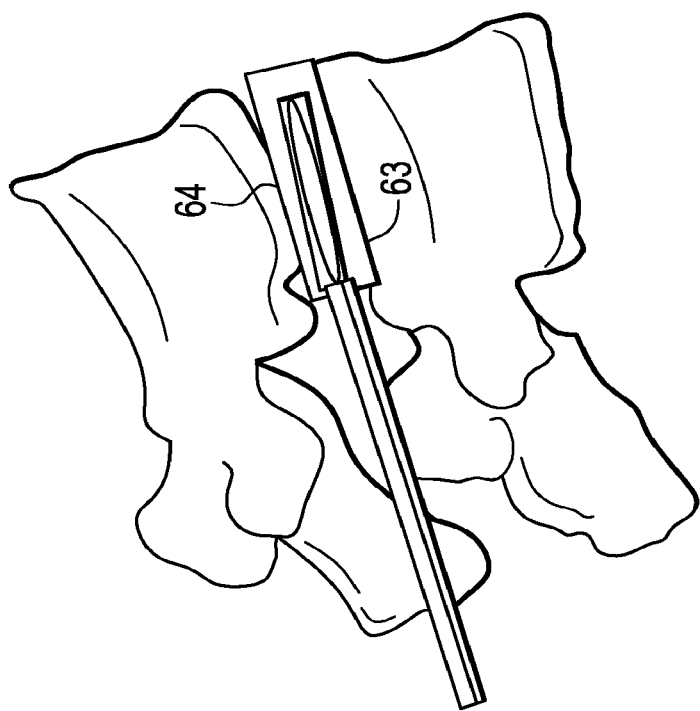
FIG. 14a-15b discloses an integrated distractor, wherein the balloon and spreader are attached.
Figure 14A:
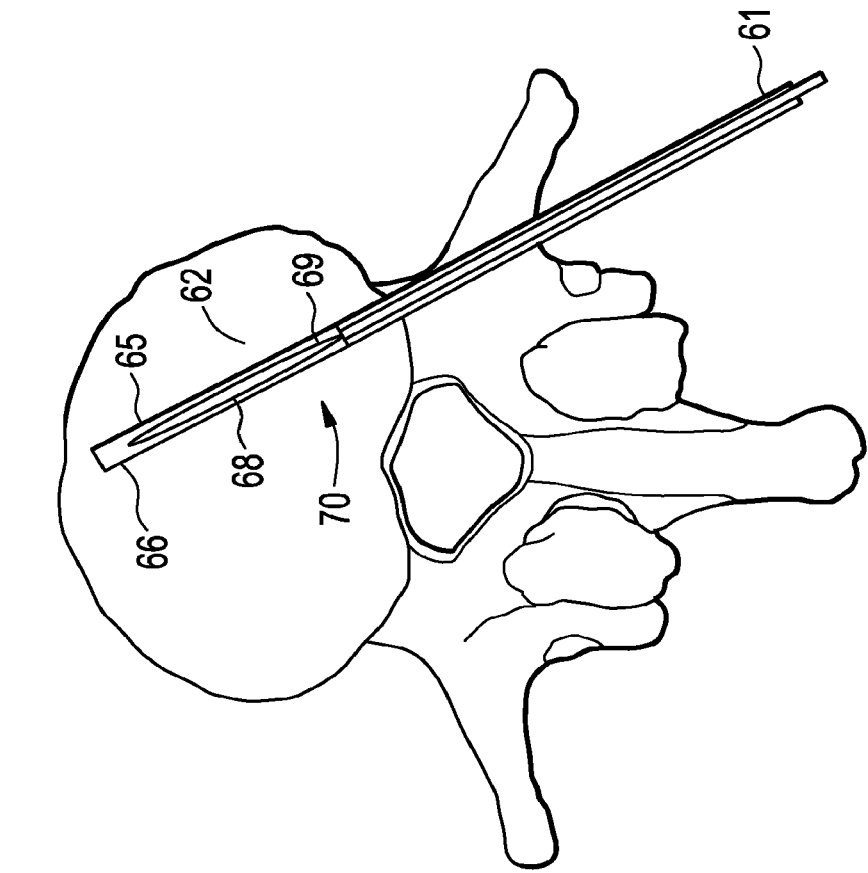
Figure 15B:
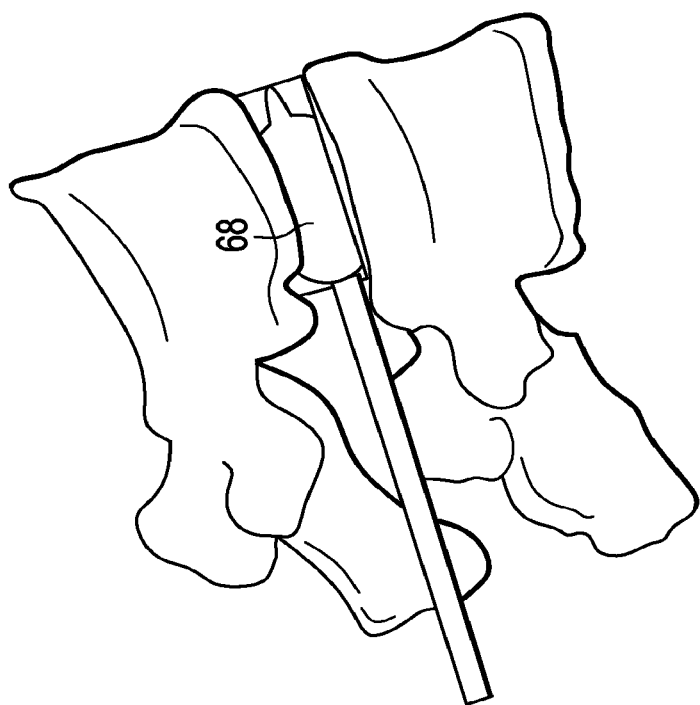
Figure 15A:
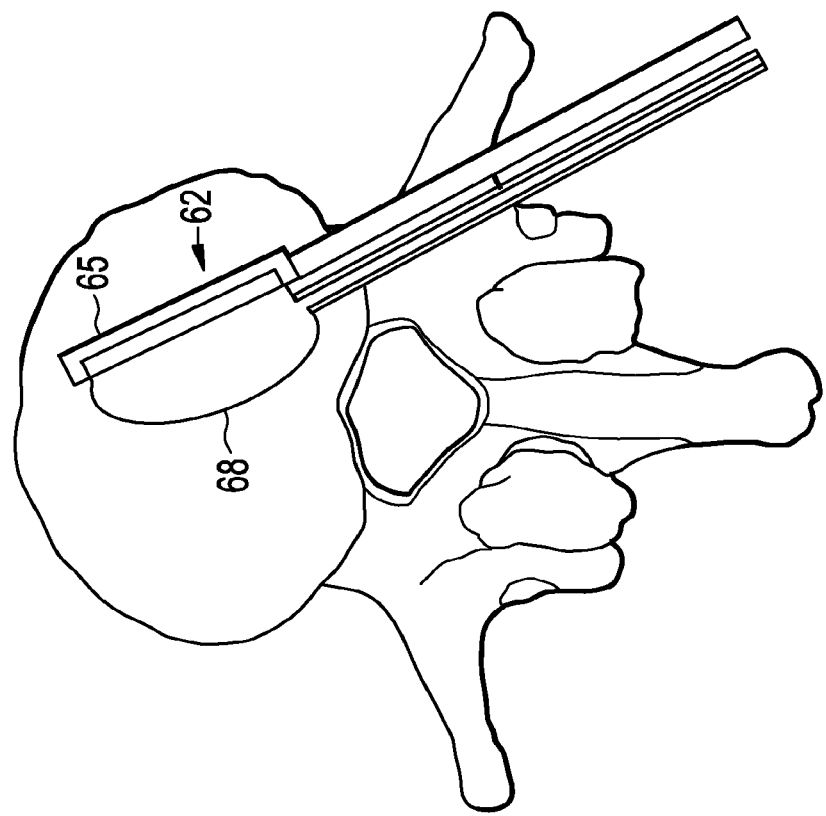

In some embodiments, the distractor of FIGS. 14a-15 b is the distal end portion of an instrument and is used to distract and clear the disc space. It is then removed from the disc space.

In some embodiments, the distractor of FIGS. 14a-15 b is the distal end portion of an implant and may be filled with a strut material to support the disc space during fusion.

In another embodiment of the present invention, and now referring to FIGS. 16a-17b, there is provided a method of treating a disc, comprising the steps of:
  a) providing an insertion device comprising i) a spreader block 80 having a height defined by first 71 and second 72 surfaces, a width defined by third 73 and fourth 74 surfaces, and a slot extending between the third and fourth surfaces, wherein the height is less than the width, and ii) an uninflated balloon 75 having a proximal portion 77 within the slot and a distal portion 76 extending outside the slot;
  b) inserting the spreader block into the disc space so that the first and second surfaces thereof contact the opposed vertebral body endplates,
  c) rotating the spreader block in the disc space so that the third and fourth surfaces thereof contact the opposed vertebral body endplates, and
  d) inflating the balloon as the third and fourth surfaces of the spreader block contact the opposed vertebral body endplates.

This method provides for use of an integrated distractor, wherein the balloon resides within a slot in the distractor.

Also in accordance with the present invention, and still referring to FIGS. 16a-17b, there is provided a distractor comprising:
  i) a spreader block having a height defined by first and second surfaces, a width defined by third and fourth surfaces, and a slot extending between the third and fourth surfaces, wherein the height is less than the width, and
  ii) an uninflated balloon having a proximal portion within the slot and a distal portion extending outside the slot;

In some embodiments, the distal portion of the balloon forms a shape when inflated that runs substantially transverse to the spreader block. Preferably, such a shape is a banana shape.

Figure 16A:
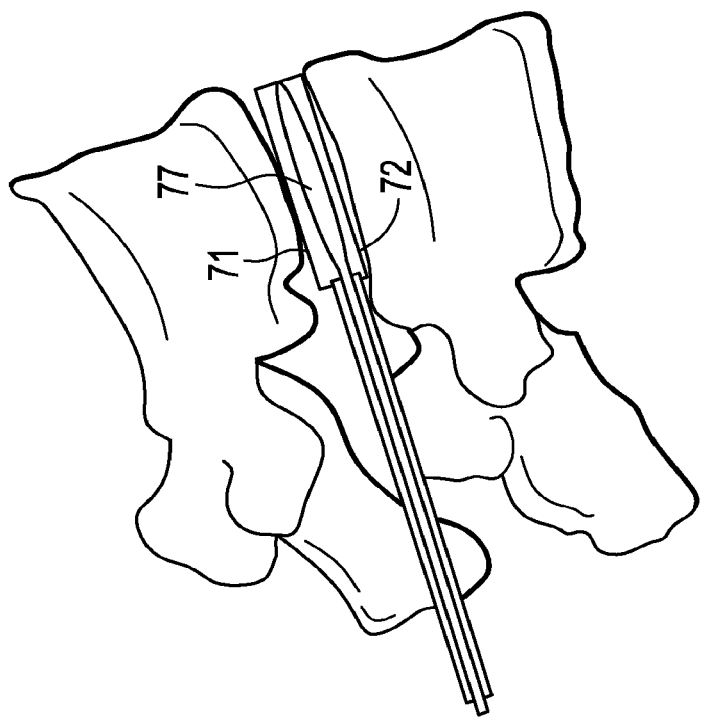
FIG. 16a-17b discloses an integrated distractor, wherein the balloon resides within a slot in the spreader.
Figure 16B:
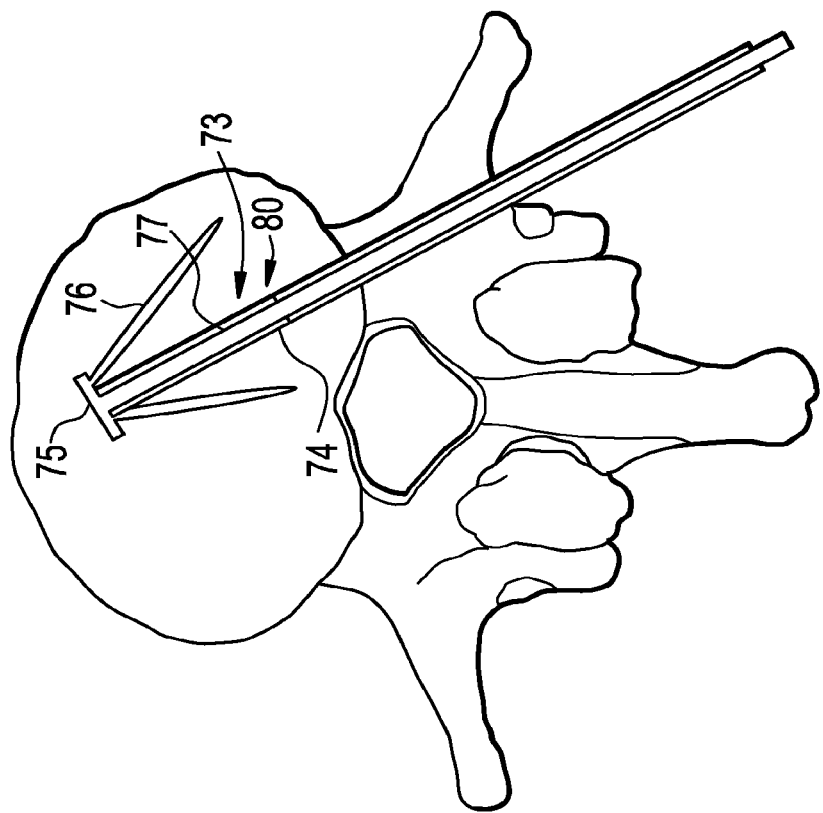
Figure 17A:
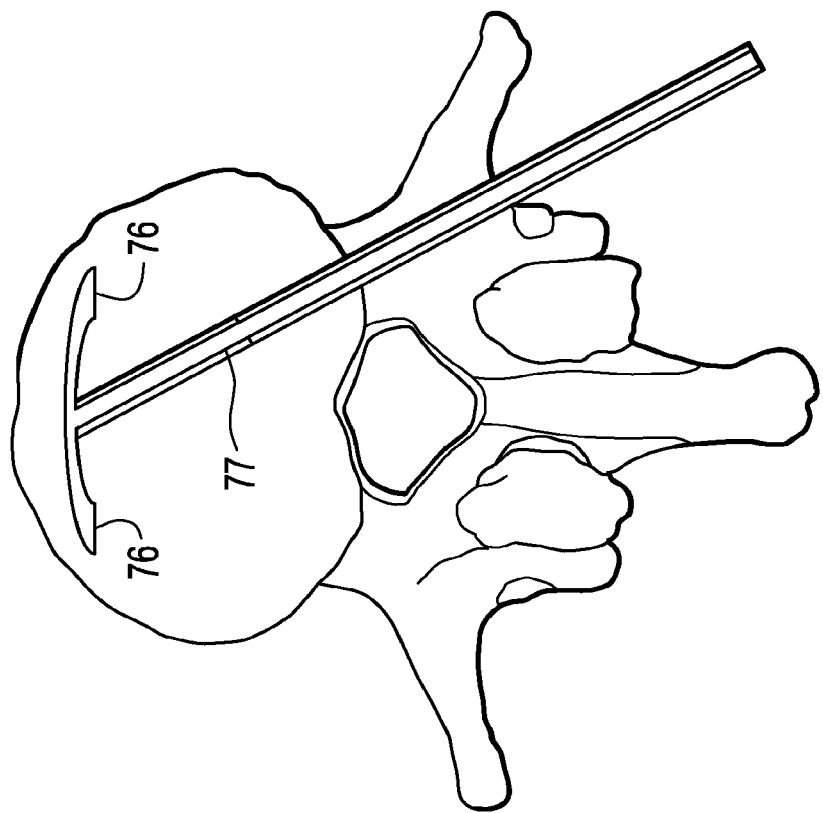
Figure 17B:
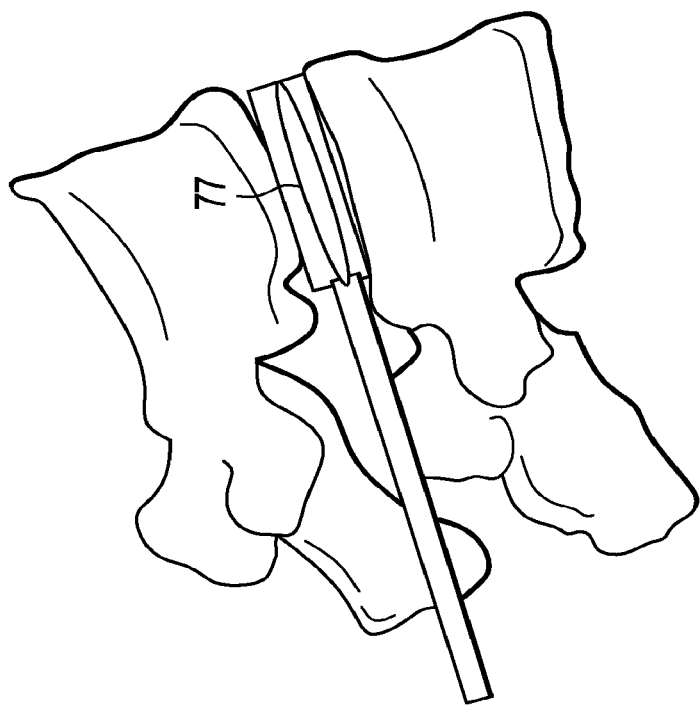

In some embodiments, the distractor of FIGS. 16a-17 b is the distal end portion of an instrument and is used to distract and clear the disc space. It is then removed from the disc space.

In some embodiments, the distractor of FIGS. 16a-17 b is the distal end portion of an implant and may be filled with a strut material to support the disc space during fusion.

In another embodiment of the present invention, and now referring to FIGS. 18a-19b, there is provided a method of treating a disc, comprising the steps of:
  a) providing an insertion device 81 comprising i) a spreader block 82 having a height defined by first 83 and second 84 surfaces, a width defined by third 85 and fourth 86 surfaces, and a slot 87 extending between the first and second surfaces, and ii) an uninflated balloon 88 having a proximal portion 89 within the slot and a distal portion 90 extending outside the slot;
  b) inserting the spreader block into the disc space so that the first and second surfaces thereof contact the opposed vertebral body endplates,
  c) inflating the balloon as the first and second surfaces of the spreader block contact the opposed vertebral body endplates.

FIG. 18a-19b discloses an integrated distractor, wherein the balloon resides within a slot in the non-rotating distractor.

Also in accordance with the present invention, and still referring to FIGS. 18a-19b, there is provided a distractor comprising:
  i) a spreader block having a height defined by first and second surfaces, a width defined by third and fourth surfaces, and a slot extending between the first and second surfaces, and
  ii) an uninflated balloon having a proximal portion within the slot and a distal portion extending outside the slot.

In some embodiments, the distal portion of the balloon forms a shape when inflated that runs substantially transverse to the spreader block. Preferably, such a shape is a banana shape.

Figure 18B:
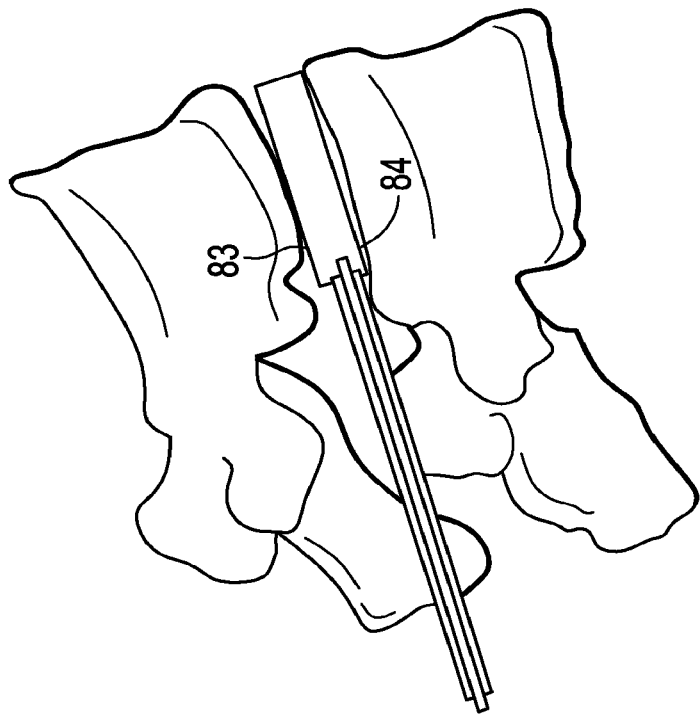
FIG. 18a-19b discloses an integrated distractor, wherein the balloon resides within a slot in the non-rotating distractor.
Figure 18A:
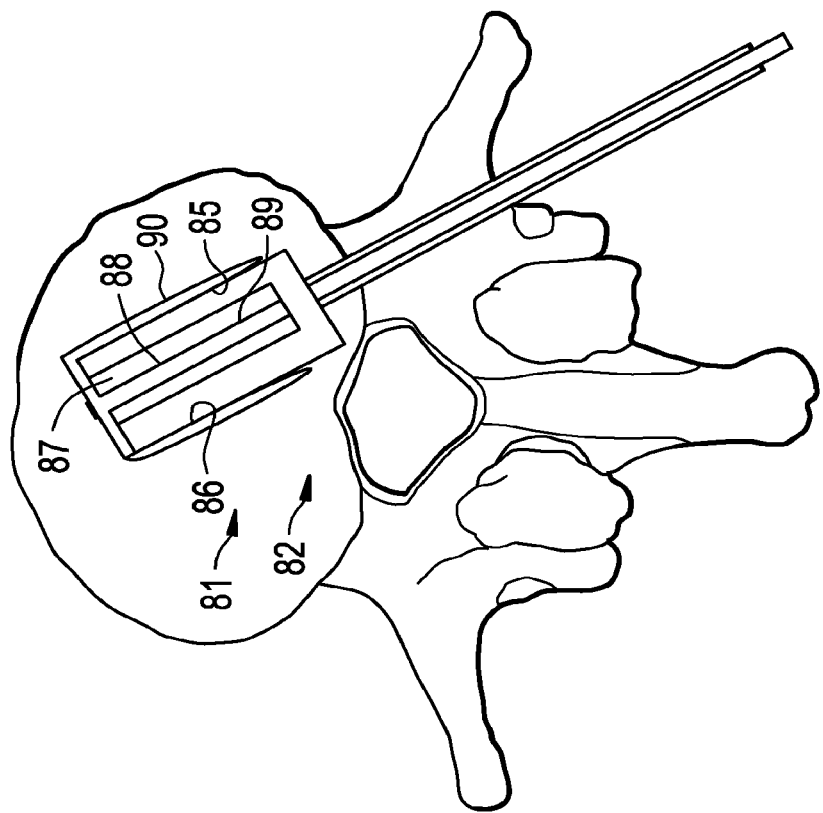
Figure 19B:
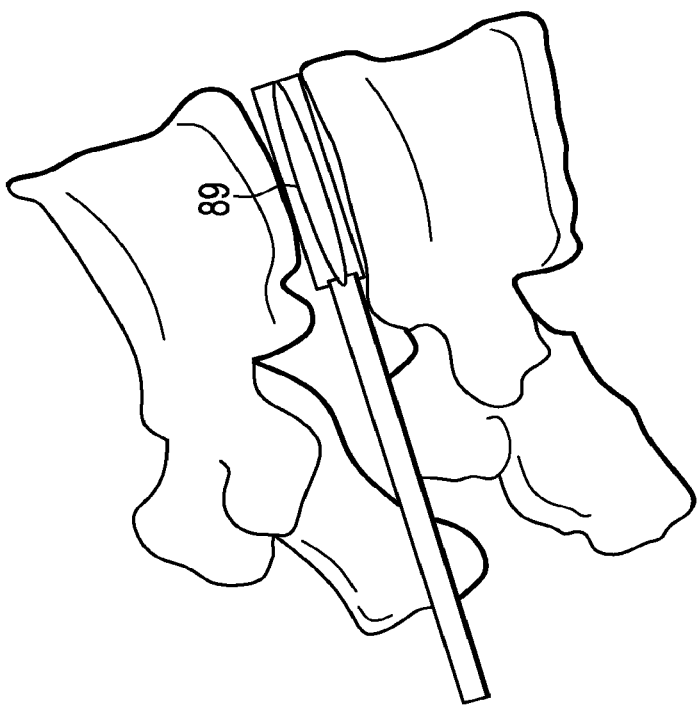
Figure 19A:
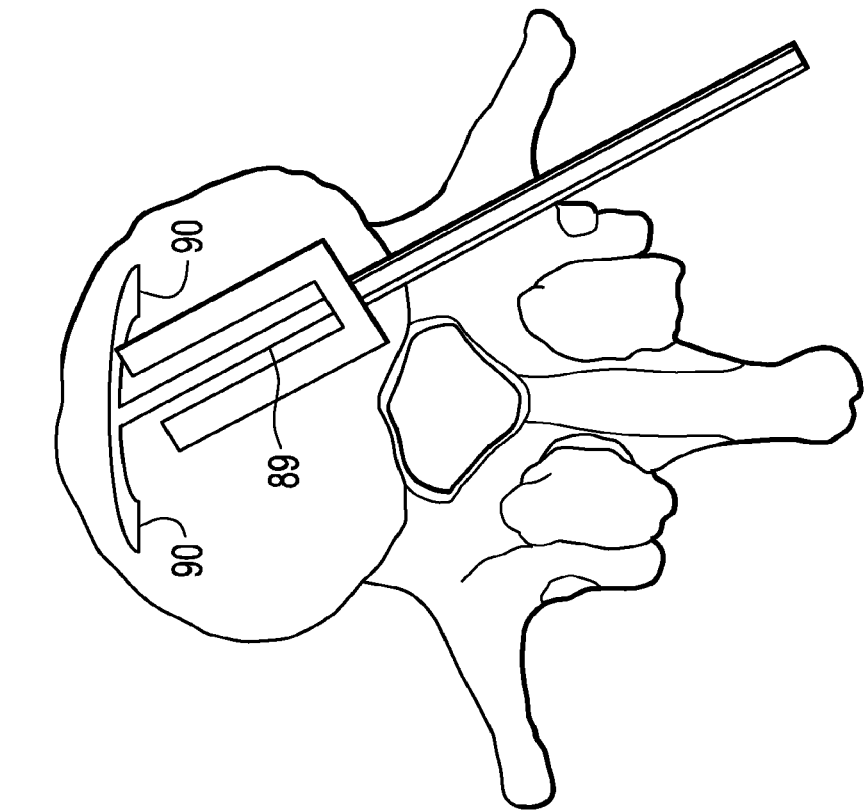

In some embodiments, the distractor of FIGS. 18a-19 b is the distal end portion of an instrument and is used to distract and clear the disc space. It is then removed from the disc space.

In some embodiments, the distractor of FIGS. 18a-19 b is the distal end portion of an implant and may be filled with a strut material to support the disc space during fusion.

In another embodiment of the present invention, and now referring to FIGS. 20a-21b, there is provided a method of treating a disc, comprising the steps of:
  a) providing a distractor comprising i) a spreader block 91 having a height defined by first 92 and second 93 surfaces, a width defined by third 94 and fourth 95 surfaces, and a slot 96 extending between the first and second surfaces, ii) a first deployable arm 97 having a proximal portion 98 hinged at a proximal end portion 111 of the spreader block on the third surface thereof and a distal portion 99, iii) a second deployable arm 101 having a proximal portion 102 hinged at the proximal end portion of the spreader block on the fourth surface thereof and a distal portion 103, and iv) an uninflated balloon 105 extending from the slot and attached to the distal portions of each deployable arm;
  b) inserting the spreader block into the disc space so that the first and second surfaces thereof contact the opposed vertebral body endplates, c) inflating the balloon as the first and second surfaces of the spreader block contact the opposed vertebral body endplates.

In this embodiment, the balloon is contained within a sectioned spreader block having deployable spreader block portions.

Also in accordance with the present invention, and still referring to FIGS. 20a-21b, there is provided a distractor comprising:
i) a spreader block having a height defined by first and second surfaces, a width defined by third and fourth surfaces, and a slot extending between the first and second surfaces,
ii) at least one arm having a proximal portion hinged at the proximal end portion of the spreader block on the third surface thereof and a distal portion,
iii) an uninflated balloon extending from the slot and attached to the distal portions of the deployable arm.

In some embodiments, the balloon forms a shape when inflated that runs substantially transverse to the spreader block. Preferably, such a shape is a banana shape.

Figure 20B:
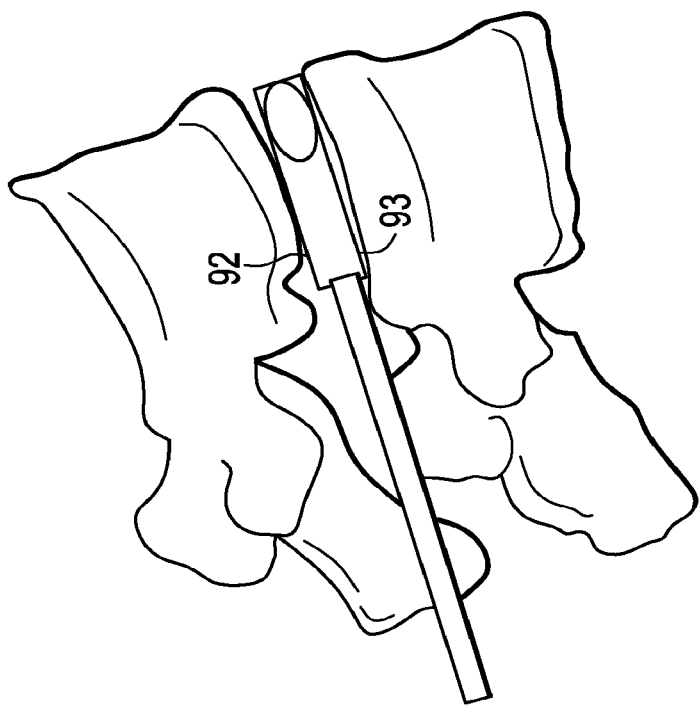
FIG. 20a-21b discloses an integrated distractor having deployable spreader block portions.
Figure 20A:
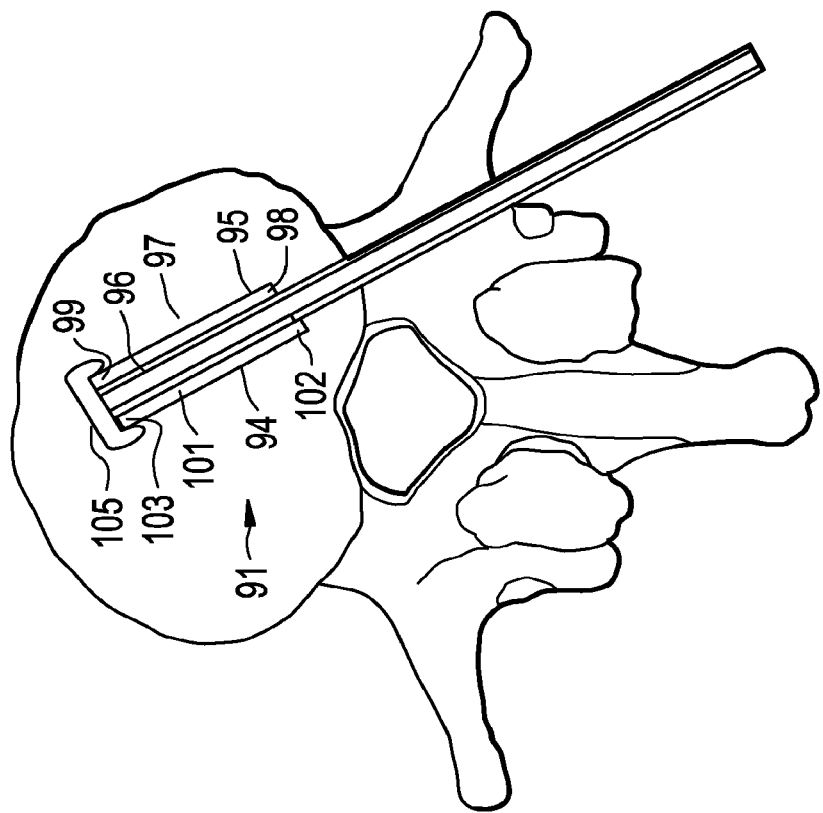
Figure 21B:
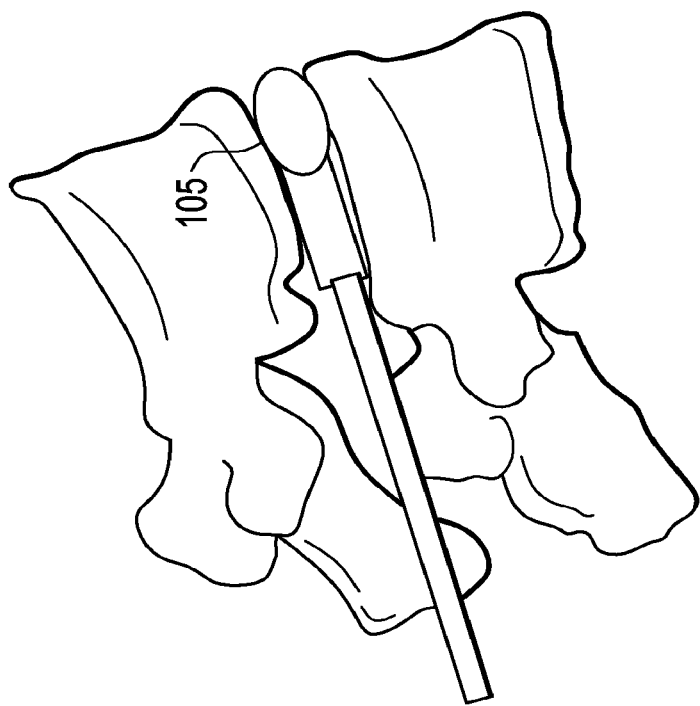
Figure 21A:
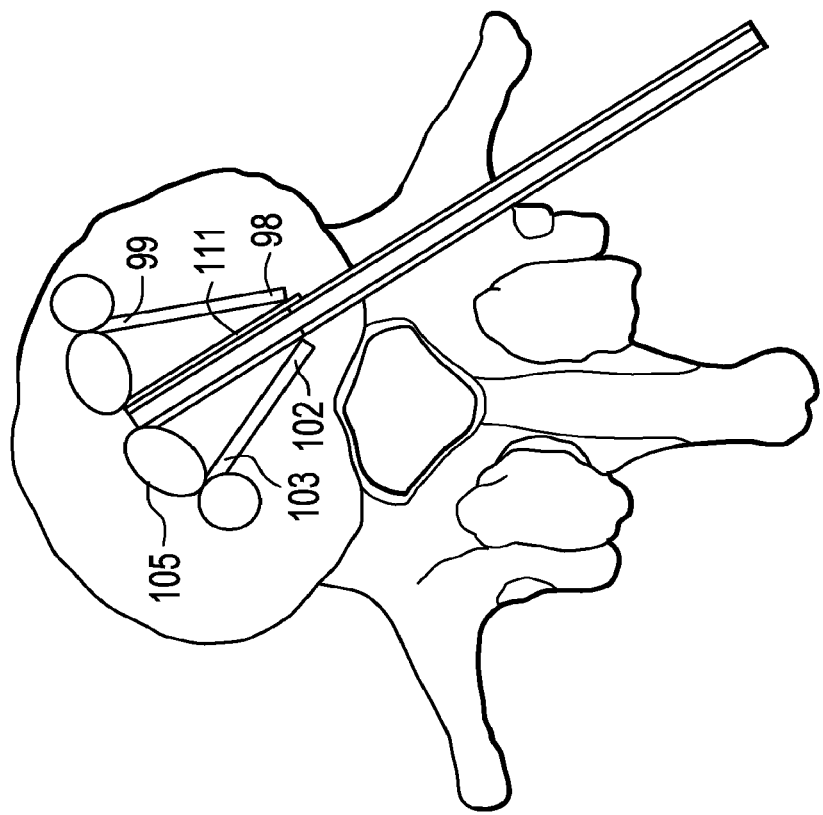

In some embodiments, the distractor of FIGS. 20a-21 b is the distal end portion of an instrument and is used to distract and clear the disc space. It is then removed from the disc space.

In some embodiments, the distractor of FIGS. 20a-21 b is the distal end portion of an implant and may be filled with a strut material to support the disc space during fusion.

The device may be made of materials typically selected for use in surgical instruments. Preferably, the entire device is sterile.

When placed in-situ (and in some instances, after curing), the flowable material that fills the balloon preferably replaces as least a portion of the natural function of the nucleus fibrosis. Accordingly, in preferred embodiments, the flowable material is a nucleus pulposus replacement. The flowable materials are preferably selected from the group consisting of liquids, gels (such as hydrogels, such as PVA-based hydrogels), and solid materials that are sufficiently morselized to flow under pressure. Typically, the liquid flowable material cures in-situ. The flowable material may cure in-situ to create a stiff material (such as polyurethane), or a relatively pliant material (such as silicone).

In other embodiments, the balloon may also be filled in accordance with the methods and materials recited in US Published Patent Application 2004/0230309, filed Feb. 13, 2004 entitled "In-situ formed intervertebral fusion device and method", the specification of which is incorporated by reference in its entirety.

We claim:

1. A surgical method, comprising:
providing a spreader having a body that has a central axis and terminates in a curved distal end portion, a first height defined between first and second surfaces proximal to the curved distal end portion, and a first width defined between third and fourth surfaces proximal to the curved distal end portion;
inserting the spreader into an intervertebral disc space, the spreader being oriented and positioned to provide clearance within the intervertebral disc space to access the intervertebral disc space, the curved distal end portion curving away from the central axis of the body along its length and substantially corresponding to a curvature of a portion of the intervertebral disc space in which the curved distal end portion is disposed;
introducing a balloon in an unexpanded state into the intervertebral disc space, the balloon being independent from the spreader;
inflating the balloon to an expanded state to maintain a size of the intervertebral disc space in an expanded configuration, at least a portion of the balloon in the expanded state contacting the curved distal end portion and at least one of the first, second, third, or fourth surfaces of the spreader, the spreader maintaining the first height and the first width throughout the inserting of the spreader and the inflating of the balloon; and
introducing an implant into the intervertebral disc space in the expanded configuration.

2. The method of claim 1, further comprising deflating the balloon to revert the balloon to its unexpanded state.

3. The method of claim 2, further comprising removing the balloon from the intervertebral disc space.

4. The method of claim 1, further comprising inserting a distracting device to support fusion of adjacent vertebrae.

5. The method of claim 1, further comprising inserting a cannula into a body of a patient, the cannula having a channel that is configured to receive one or more substances for inflating the balloon therethrough.

6. The method of claim 5, further comprising removing the cannula from the body of the patient.

7. The method of claim 5, wherein the spreader is advanced distal to the cannula when disposed in the body of the patient.

8. The method of claim 1, wherein the balloon contacts one of the first or second surfaces of the spreader while an opposite surface of the first or second surfaces does not contact the balloon.

9. The method of claim 1, wherein the introducing of the balloon in the unexpanded state into the intervertebral disc space further comprises inserting the balloon adjacent the spreader.

10. A surgical method, comprising:
inserting a spreader having a constant height defined between first and second surfaces, and a constant width defined between third and fourth surfaces into an intervertebral disc space, the spreader being oriented and positioned to provide clearance within the intervertebral disc space to access the intervertebral disc space;
introducing a balloon in an unexpanded state that is not physically joined together with the spreader into the intervertebral disc space along the spreader such that at least one of opposed surfaces of the balloon is not circumferentially surrounded by the spreader throughout the introduction of the balloon into the intervertebral disc space;
inflating the balloon to an expanded state to maintain a size of the intervertebral disc space, at least a portion of the balloon in the expanded state contacting at least one of the first, second, third, or fourth surfaces of the spreader, the balloon in the expanded state pushing against adjacent vertebrae to maintain the size of the intervertebral disc space; and
inserting a cannula into a body of a patient, the cannula having a channel that is configured to receive one or more substances for inflating the balloon therethrough and being capable of translating independent of the spreader, an outer surface of the cannula passing laterally outside an outer surface of a proximal handle of the spreader during the insertion of the cannula into the body of the patient.

11. The method of claim 10, wherein a circumference of the balloon in the expanded state lies external to the height and the width of the spreader when disposed in the intervertebral disc space.

12. The method of claim 10, further comprising rotating the spreader to increase a distance between the adjacent vertebrae of the intervertebral disc space.

13. The method of claim 12, wherein the spreader is rotated approximately 90 degrees.

14. The method of claim 10, further comprising filling the balloon with any of bone cement, osteoinductive cement, bone particles, bone substitutes, growth factors, BMP, viscous gels, curable elastomers, or hydrogels.

* * * * *